US009856530B2

(12) United States Patent
Hindson et al.

(10) Patent No.: US 9,856,530 B2
(45) Date of Patent: *Jan. 2, 2018

(54) METHODS AND SYSTEMS FOR PROCESSING POLYNUCLEOTIDES

(71) Applicant: 10X Genomics, Inc., Pleasanton, CA (US)

(72) Inventors: Benjamin Hindson, Pleasanton, CA (US); Serge Saxonov, Oakland, CA (US); Kevin Ness, Boulder, CO (US); Paul Hardenbol, San Francisco, CA (US); Michael Schnall-Levin, San Francisco, CA (US); Mirna Jarosz, Palo Alto, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,519

(22) Filed: May 5, 2017

(65) Prior Publication Data

US 2017/0247757 A1    Aug. 31, 2017

Related U.S. Application Data

(63) Continuation of application No. 15/376,582, filed on Dec. 12, 2016, now Pat. No. 9,701,998, which is a continuation-in-part of application No. 14/104,650, filed on Dec. 12, 2013, now Pat. No. 9,567,631, said application No. 15/376,582 is a continuation-in-part of application No. 14/250,701, filed on Apr. 11, 2014, now abandoned, which is a continuation of application No. 14/175,973, filed on Feb. 7, 2014, now Pat. No. 9,388,465.

(60) Provisional application No. 61/737,374, filed on Dec. 14, 2012, provisional application No. 61/844,804, filed on Jul. 10, 2013, provisional application No. 61/840,403, filed on Jun. 27, 2013, provisional application No. 61/800,223, filed on Mar. 15, 2013, provisional application No. 61/762,435, filed on Feb. 8, 2013.

(51) Int. Cl.
*C12Q 1/68* (2006.01)

(52) U.S. Cl.
CPC ........ *C12Q 1/6874* (2013.01); *C12Q 1/6806* (2013.01)

(58) Field of Classification Search
None
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Kessler |
| 3,479,141 A | 11/1969 | William et al. |
| 4,253,846 A | 3/1981 | Smythe et al. |
| 4,582,802 A | 4/1986 | Zimmerman et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,436,130 A | 7/1995 | Mathies et al. |
| 5,489,523 A | 2/1996 | Mathur |
| 5,512,131 A | 4/1996 | Kumar et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,958,703 A | 9/1999 | Dower et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |

(Continued)

FOREIGN PATENT DOCUMENTS

| | | |
|---|---|---|
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1594980 B1 | 11/2009 |
| EP | 1967592 B1 | 4/2010 |
| EP | 2258846 A2 | 12/2010 |

(Continued)

OTHER PUBLICATIONS

Abate, et al. Beating Poisson encapsulation statistics using close-packed ordering. Lab Chip. Sep. 21, 2009;9(18):2628-31. doi: 10.1039/b909386a. Epub Jul. 28, 2009.

(Continued)

*Primary Examiner* — David C Thomas
(74) *Attorney, Agent, or Firm* — Wilson Sonsini Goodrich & Rosati

(57) ABSTRACT

The present disclosure provides compositions, methods, systems, and devices for polynucleotide processing. Such polynucleotide processing may be useful for a variety of applications, including polynucleotide sequencing.

30 Claims, 8 Drawing Sheets

(56) References Cited

U.S. PATENT DOCUMENTS

| | | |
|---|---|---|
| 6,057,107 A | 5/2000 | Fulton |
| 6,057,149 A | 5/2000 | Burns et al. |
| 6,103,537 A | 8/2000 | Ullman et al. |
| 6,143,496 A | 11/2000 | Brown et al. |
| 6,171,850 B1 | 1/2001 | Nagle et al. |
| 6,172,218 B1 | 1/2001 | Brenner |
| 6,265,552 B1 | 7/2001 | Schatz |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,133,719 B2 | 3/2012 | Drmanac et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,563,274 B2 | 10/2013 | Brenner et al. |
| 8,592,150 B2 | 11/2013 | Drmanac et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,986,286 B2 | 3/2015 | Tanghoej et al. |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,102,980 B2 | 8/2015 | Brenner et al. |
| 9,249,460 B2 | 2/2016 | Pushkarev et al. |
| 9,290,808 B2 | 3/2016 | Fodor et al. |
| 9,347,059 B2 | 5/2016 | Saxonov |
| 9,388,465 B2 | 7/2016 | Hindson et al. |
| 9,410,201 B2 * | 8/2016 | Hindson .............. C12Q 1/6874 |
| 9,567,631 B2 | 2/2017 | Hindson et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 * | 7/2017 | Hindson .............. C12Q 1/6806 |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027221 A1 | 2/2003 | Scott et al. |
| 2003/0028981 A1 | 2/2003 | Chandler et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |

(56) References Cited

U.S. PATENT DOCUMENTS

| | | |
|---|---|---|
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0210479 A1 | 8/2010 | Griffiths et al. |
| 2010/0248237 A1 | 9/2010 | Froehlich et al. |
| 2011/0000560 A1 | 1/2011 | Miller et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0190032 A1 | 7/2012 | Ness et al. |
| 2012/0196288 A1 | 8/2012 | Beer et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0309002 A1 | 12/2012 | Link |
| 2012/0316074 A1 | 12/2012 | Saxonov |
| 2013/0018970 A1 | 1/2013 | Woundy et al. |
| 2013/0028812 A1 | 1/2013 | Prieto et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |

(56) References Cited

U.S. PATENT DOCUMENTS

| | | |
|---|---|---|
| 2013/0178368 A1 | 7/2013 | Griffiths et al. |
| 2013/0189700 A1 | 7/2013 | So et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0274117 A1 | 10/2013 | Church et al. |
| 2013/0296173 A1 | 11/2013 | Callow et al. |
| 2013/0343317 A1 | 12/2013 | Etemad et al. |
| 2014/0057799 A1 | 2/2014 | Johnson et al. |
| 2014/0065234 A1 | 3/2014 | Shum et al. |
| 2014/0120529 A1 | 5/2014 | Andersen et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0072899 A1 | 3/2015 | Ward et al. |
| 2015/0111256 A1 | 4/2015 | Church et al. |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0353999 A1 | 12/2015 | Agresti et al. |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0032282 A1 | 2/2016 | Vigneault et al. |
| 2016/0122817 A1 | 5/2016 | Jarosz et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0257984 A1 | 9/2016 | Hardenbol et al. |
| 2016/0281160 A1 | 9/2016 | Jarosz et al. |
| 2016/0304860 A1 | 10/2016 | Hindson et al. |
| 2016/0348093 A1 | 12/2016 | Price et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0260584 A1 | 9/2017 | Zheng et al. |

FOREIGN PATENT DOCUMENTS

| | | |
|---|---|---|
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2752664 A1 | 7/2014 |
| GB | 2097692 B | 5/1985 |
| GB | 2485850 A | 5/2012 |
| JP | 55949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009208074 A | 9/2009 |
| WO | WO-8402000 A1 | 5/1984 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9952708 A1 | 10/1999 |
| WO | WO-0008212 A1 | 2/2000 |
| WO | WO-0023181 A1 | 4/2000 |
| WO | WO-0026412 A1 | 5/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007089541 A2 | 8/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A3 | 11/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009048532 A2 | 4/2009 |
| WO | WO-2009061372 A1 | 5/2009 |
| WO | WO-2009085215 A1 | 7/2009 |
| WO | WO-2010004018 A2 | 1/2010 |
| WO | WO-2010033200 A2 | 3/2010 |

(56) References Cited

FOREIGN PATENT DOCUMENTS

| WO | WO-2010104604 A1 | 9/2010 |
|---|---|---|
| WO | WO-2010115154 A1 | 10/2010 |
| WO | WO-2010148039 A2 | 12/2010 |
| WO | WO-2010151776 A1 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011140627 A1 | 11/2011 |
| WO | WO-2012012037 A1 | 1/2012 |
| WO | WO-2012048341 A1 | 4/2012 |
| WO | WO-2012083225 A2 | 6/2012 |
| WO | WO-2012106546 A2 | 8/2012 |
| WO | WO-2012112970 A2 | 8/2012 |
| WO | WO-2012136734 A1 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012166425 A2 | 12/2012 |
| WO | WO-2013019751 A1 | 2/2013 |
| WO | WO-2013036929 A1 | 3/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2014028537 A1 | 2/2014 |
| WO | WO-2014074611 A1 | 5/2014 |
| WO | WO-2014093676 A1 | 6/2014 |
| WO | WO-2014144495 A1 | 9/2014 |
| WO | WO-2014210353 A2 | 12/2014 |
| WO | WO-2015044428 A1 | 4/2015 |
| WO | WO-2015164212 A1 | 10/2015 |
| WO | WO-2016040476 A1 | 3/2016 |
| WO | WO-2017053905 A1 | 3/2017 |
| WO | WO-2017075265 A1 | 5/2017 |

OTHER PUBLICATIONS

Abate, et al. High-throughput injection with microfluidics using picoinjectors. Proc Natl Acad Sci U S A. Nov. 9, 2010;107(45):19163-6. doi: 10.1073/pnas.1006888107. Epub Oct. 20, 2010.
Abate et al., Valve-based flow focusing for drug formation. Appl Phys Lett. 2009;94. 3 pages.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Aitman, et al. Copy number polymorphism in Fcgr3 predisposes to glomerulonephritis in rats and humans. Nature. Feb. 16, 2006;439(7078):851-5.
Akselband. Enrichment of slow-growing marine microorganisms from mixed cultures using gel microdrop (GMD) growth assay and fluorescence-activated cell sorting. J. Exp. Marine Bioi., 329: 196-205 (2006).
Akselband. Rapid mycobacteria drug susceptibility testing using gel microdrop (GMD) growth assay and flow cytometry. J. Microbiol. Methods, 62:181-197 (2005).
Altemos et al. Genomic Characterization of Large Heterochromatic Gaps in the Human Genome Assembly. PLOS Computational Biology, May 15, 2014, vol. 10, Issue 5, 14 pages.
Amini, S. et al. Haplotype-resolved whole-genome sequencing by contiguity-preserving transposition and combinatorial indexing. Nature Genetics (2014) 46:1343-1349 doi:10.1038/ng.3119.
Anna, S.L., et al. Formation of dispersions using "flow focusing" in microchannels. Applied Physics Letters, vol. 82, No. 3, pp. 364-366 (2003).

Anonymous, "Oligo(dT)25 cellulose beads" NEB (2012) Retrieved from the Internet:https://www.neb.com/~/media/Catalog/All-Products/286CA51268E24DE1B06F1CB2886981354/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Attia, et al. Micro-injection moulding of polymer microfluidic devices. Microfluidics and Nanofluidics. 2009; 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.
Berkum, et al. Hi-C: a method to study the three-dimensional architecture of genomes. J Vis Exp. May 6, 2010;(39). pii: 1869. doi: 10.3791/1869.
Biles et al., Nucl. Acids Res. 32(22):e176 2004.
Bodi, K. et al. Comparison of Commercially Available Target Enrichment Methods for Next-Generation Sequencing. J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al. Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Briggs, et al. Tumor-infiltrating immune repertoires captures by single-cell barcoding in emulsion with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Browning, et al. Haplotype phasing: existing methods and new developments. Nat Rev Genet. Sep. 16, 2011;12(10):703-14. doi: 10.1038/nrg3054. Review.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll. The selection of high-producing cell lines using flow cytometry and cell sorting. Exp. Op. Biol. Therap., 4:11 1821-1829 (2004).
Chaudhary. A rapid method of cloning functional variable-region antibody genese in *Escherichia coli* as single-chain imrnunotoxins. Proc. Natl. Acad. Sci USA 87: 1066-1070 (Feb. 1990).
Chechetkin et al. Sequencing by hybridization with the generic 6-mer oligonucleotide microarray: an advanced scheme for data processing. J Biomol Struct Dyn. Aug. 2000;18(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Christian M, et al. Targeting DNA double-strand breaks with TAL effector nucleases. Genetics. 2010;186:757-761.

(56) References Cited

OTHER PUBLICATIONS

Christiansen et al. The Covalent Eukaryotic Topoisomerase I-DNA Intermediate Catalyzes pH-dependent Hydrolysis and Alcoholysis. J Biol Chem (Apr. 14, 1994) 269(15):11367-11373.

Chu, et al. Controllable monodisperse multiple emulsions. Angew Chem Int Ed Engl. 2007;46(47):8970-4.

Chung, et al. Structural and molecular interrogation of intact biological systems. Nature. May 16, 2013;497(7449):332-7. doi: 10.1038/nature12107. Epub Apr. 10, 2013.

Clausell-Tormos et al. Droplet-based microfluidic platforms for the encapsulation and screening of mammalian cells and multicellular organisms. Chem. Biol. 15:427-437 (2008).

Cong, et al. Multiplex genome engineering using CRISPR/Cas systems. Science. Feb. 15, 2013;339(6121):819-23. doi: 10.1126/science.1231143. Epub Jan. 3, 2013.

Cook, et al. Copy-number variations associated with neuropsychiatric conditions. Nature. Oct. 16, 2008;455(7215):919-23. doi: 10.1038/nature07458.

Co-pending U.S. Appl. No. 15/355,542, filed Nov. 18, 2016.
Co-pending U.S. Appl. No. 15/392,557, filed Dec. 28, 2016.
Co-pending U.S. Appl. No. 15/430,298, filed Feb. 10, 2017.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/470,814, filed Mar. 27, 2017.
Co-pending U.S. Appl. No. 15/588,519, filed May 5, 2017.

Coufal, et al. L1 retrotransposition in human neural progenitor cells. Nature. Aug. 27, 2009;460(7259):1127-31. doi: 10.1038/nature08248. Epub Aug. 5, 2009.

De Bruin et al., UBS Investment Research. Q-Series®: DNA Sequencing. UBS Securities LLC. Jul. 12, 2007. 15 pages.

Dekker, et al. Capturing chromosome conformation. Science. Feb. 15, 2002;295(5558):1306-11.

Demirci, et al. Single cell epitaxy by acoustic picolitre droplets. Lab Chip. Sep. 2007;7(9):1139-45. Epub Jul. 10, 2007.

Doerr. The smallest bioreactor. Nature Methods, 2:5 326 (2005).

Doshi, et al. Red blood cell-mimicking synthetic biomaterial particles. Proceedings of the National Academy of Sciences 106.51 (2009): 21495-21499.

Dowding, et al. Oil core/polymer shell microcapsules by internal phase separation from emulsion droplets. II: controlling the release profile of active molecules. Langmuir. Jun. 7, 2005;21(12):5278-84.

Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.

Dressler, et al. Droplet-based microfluidics enabling impact on drug discovery. J Biomol Screen. Apr. 2014;19(4):483-96. doi: 10.1177/1087057113510401. Epub Nov. 15, 2013.

Dressman et al. Transforming single DNA molecules into fluorescent magnetic particles for detection and enumeration of genetic variations. Proc. Natl. Acad. Sci. 2003. 100(15):8817-8822.

Drmanac et al., Sequencing by hybridization (SBH): advantages, achievements, and opportunities. Adv Biochem Eng Biotechnol. 2002;77 :75-101.

Droplet Based Sequencing (slides) dated (Mar. 12, 2008).

Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.

Esser-Kahn, et al. Triggered release from polymer capsules. Macromolecules. 2011; 44:5539-5553.

Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.

Fan, et al. Noninvasive diagnosis of fetal aneuploidy by shotgun sequencing DNA from maternal blood. Proc Natl Acad Sci U S A. Oct. 21, 2008;105(42):16266-71. doi: 10.1073/pnas.0808319105. Epub Oct. 6, 2008.

Fan, et al. Whole-genome molecular haplotyping of single cells. Nature Biotechnology, vol. 29, No. 1. Jan. 1, 2011. pp. 51-57.

Fang, et al. Fluoride-cleavable biotinylation phosphoramidite for 5'-end-labeling and affinity purification of synthetic oligonucleotides. Nucleic Acids Res. Jan. 15, 2003;31(2):708-15.

Fisher, et al. A scalable, fully automated process for construction of sequence-ready human exome targeted capture libraries. Genome Biol. 2011;12(1):R1. doi: 10.1186/gb-2011-12-1-rl. Epub Jan. 4, 2011.

Frampton, G.M. et al. Development and validation of a clinical cancer genomic profiling test based on massively parallel DNA sequencing. Nature Biotechnology (2013) 31(11):1023-1031. doi:10.1038/nbr.2696.

Fredrickson, et al. Macro-to-micro interfaces for microfluidic devices. Lab Chip. Dec. 2004;4(6):526-33. Epub Nov. 10, 2004.

Freiberg, et al. Polymer microspheres for controlled drug release. Int J Pharm. Sep. 10, 2004;282(1-2):1-18.

Fu, A.Y., et al. A microfabricated fluorescence-activated cell sorter. Nature Biotechnology, vol. 17, pp. 1109-1111 (1999).

Fulton et al., Advanced multiplexed analysis with the FlowMetrix system. Clin Chern. Sep. 1997;43(9): 1749-56.

Garstecki, et al. Formation of monodisperse bubbles in a microfluidic flow-focusing device. Applied Physics Letters. 2004; 85(13):2649-2651. DOI: 10.1063/1.1796526.

Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.

Gericke, et al. Functional cellulose beads: preparation, characterization, and applications. Chemical reviews 113.7 (2013): 4812-4836.

Ghadessy, et al. Directed evolution of polymerase function by compartmentalized self-replication. Proc Natl Acad Sci U S A. Apr. 10, 2001;98(8):4552-7. Epub Mar. 27, 2001.

Gonzalez, et al. The influence of CCL3L1 gene-containing segmental duplications on HIV-1/AIDS susceptibility. Science. Mar. 4, 2005;307(5714):1434-40. Epub Jan. 6, 2005.

Granieri, Lucia. Droplet-based microfluidics and engineering of tissue plasminogen activator for biomedical applications. Ph.D. Thesis, Nov. 13, 2009 (131 pages).

Grasland-Mongrain, et al. Droplet coalescence in microfluidic devices. Jan.-Jul. 2003. 31 pages. http://www.eleves.ens.fr/home/grasland/rapports/stage4.pdf.

Guo, et al. Droplet microfluidics for high-throughput biological assays. Lab Chip. Jun. 21, 2012;12(12):2146-55. doi: 10.1039/c2lc21147e. Epub Feb. 9, 2012.

Gyarmati, et al. Reversible disulphide formation in polymer networks: a versatile functional group from synthesis to applications. European Polymer Journal. 2013; 49:1268-1286.

Hashimshony, et al. CEL-Seq: Single-Cell RNa-Seq by Multiplexed Linear Amplification. Cell Rep. Sep. 27, 2012;2(3):666-73. doi: 10.1016/j.celrep.2012.08.003. Epub Aug. 30, 2012.

He. Selective Encapsulation of Single Cells and Subcellular Organelles into Picoliter- and Femtoliter-Volume Droplets. Anal. Chem 77: 1539-1544 (2005).

He, J. et al. Genotyping-by-sequencing (GBS), an ultimate marker-assisted selections (MAS) tool to accelerate plant breeding. Frontiers in Plant Sci (Sep. 30, 2014) 5:1-8.

Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.

Holtze, et al. Biocompatible surfactants for water-in-fluorocarbon emulsions. Lab Chip. Oct. 2008;8(10):1632-9. doi: 10.1039/b806706f. Epub Sep. 2, 2008.

Huebner. Quantitative detection of protein expression in single cells using droplet microfluidics. Chem. Commun. 1218-1220 (2007).

Hug, et al. Measurement of the number of molecules of a single mRNA species in a complex mRNA preparation. J Theor Biol. Apr. 21, 2003;221(4):615-24.

Sigma. *Streptavidin-agarose* (S1638) product information sheet. www.sigma-aldrich.com.

Illumina Nextera Enrichment Sample Preparation Guide. Feb. 2013.

Illumina TruSeq Custom Enrichment Kit Data Sheet. (c) 2014.

(56) References Cited

OTHER PUBLICATIONS

Ioannidis, N. Manufacturing of Agarose-Based Chromatographic Adsorbents With Controlled Pore and Particle Sizes. A thesis submitted to the University of Birmingham for the degree of Doctor of Philosophy. 2009.

Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.

Jung, et al. Micro machining of injection mold inserts for fluidic channel of polymeric biochips. Sensors. 2007; 7(8):1643-1654.

Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.

Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.

Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.

Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.

Khomiakov A et al. Analysis of perfect and mismatched DNA duplexes by a generic hexanucleotide microchip. Mol Bioi (Mosk). Jul.-Aug. 2003;37(4):726-41. Russian. Abstract only.

Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.

Kim, et al. Fabrication of monodisperse gel shells and functional microgels in microfluidic devices. Angew Chem Int Ed Engl. 2007;46(11):1819-22.

Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.

Kitzman, et al. Noninvasive whole-genome sequencing of a human fetus. Sci Transl Med. Jun. 6, 2012;4(137):137ra76. doi: 10.1126/scitranslmed.3004323.

Kivioj a, et al. Counting Absolute Numbers of Molecules Using Unique Molecular Identifiers. Nature Methods 9, 72-74 (2012).

Klein, et al. Droplet barcoding for single-cell transcriptomics applied to embryonic stem cells. Cell. May 21, 2015;161(5):1187-201. doi: 10.1016/j.cell.2015.04.044.

Knight, et al. Subtle chromosomal rearrangements in children with unexplained mental retardation. Lancet. Nov. 13, 1999;354(9191):1676-81.

Korlach et al., Methods in Enzymology, Real-Time DNA Sequencing from Single Polymerase Molecules, (2010) 472:431-455.

Koster et al. Drop-based microfluidic devices for encapsulation of single cells. Lab on a Chip The Royal Soc. of Chem. 8: 1110-1115 (2008).

Kutyavin, et al. Oligonucleotides containing 2-aminoadenine and 2-thiothymine act as selectively binding complementary agents. Biochemistry. Aug. 27, 1996;35(34):11170-6.

Lagus, et al. A review of the theory, methods and recent applications of high-throughput single-cell droplet microfluidics. J. Phys. D: Appl. Phys. (2013) 46:114005. (21 pages).

Lee, et al. ACT-PRESTO: Rapid and consistent tissue clearing and labeling method for 3-dimensional (3D) imaging. Sci Rep. Jan. 11, 2016;6:18631. doi: 10.1038/srep18631.

Lee; et al. Highly multiplexed subcellular RNA sequencing in situ. Science. Mar. 21, 2014;343(6177):1360-3. doi: 10.1126/science.1250212. Epub Feb. 27, 2014.

Lee, J-H. et al. Fluorescent in situ sequencing (FISSEQ) of RNA for gene expression profiling in intact cells and tissues. Nature Protocols (Feb. 12, 2015) 10(3):442-458.

Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].

Li, Y., et al. PEGylated PLGA Nanoparticles as protein carriers: synthesis, preparation and biodistribution in rats. Journal of Controlled Release, vol. 71, pp. 203-211 (2001).

Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.

Liu, et al. Smart thermo-triggered squirting capsules for Nanoparticle delivery. Soft Matter. 2010; 6(16):3759-3763.

Loscertales, I.G., et al. Micro/Nano Encapsulation via Electrified Coaxial Liquid Jets. Science, vol. 295, pp. 1695-1698 (2002).

Love. A microengraving method for rapid selection of single cells producing antigen-specific antibodies. Nature Biotech, 24:6 703 (Jun. 2006).

Lowe, Adam J. Norbornenes and [n]polynorbornanes as molecular scaffolds for anion recognition. Ph.D. Thesis (May 2010). (361 pages).

Lupski. Genomic rearrangements and sporadic disease. Nat Genet. Jul. 2007;39(7 Suppl):S43-7.

Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.

Mair, et al. Injection molded microfluidic chips featuring integrated interconnects. Lab Chip. Oct. 2006;6(10):1346-54. Epub Jul. 31, 2006.

Makino, et al. Preparation of hydrogel microcapsules: Effects of preparation conditions upon membrane properties. Colloids and Surfaces B: Biointerfaces. Nov. 1998; 12(2), 97-104.

Marcus. Gene method offers diagnostic hope. The Wall Street Journal. Jul. 11, 2012.

Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.

Mazutis, et al. Selective droplet coalescence using microfluidic systems. Lab Chip. Apr. 24, 2012;12(10):1800-6. doi: 10.1039/c2lc40121e. Epub Mar. 27, 2012.

Merriman, et al. Progress in ion torrent semiconductor chip based sequencing. Electrophoresis. Dec. 2012;33(23):3397-417. doi: 10.1002/elps.201200424.

Microfluidic ChipShop. Microfluidic product catalogue. Mar. 2005.
Microfluidic ChipShop. Microfluidic product catalogue. Oct. 2009.

Miller JC, et al. An improved zinc-finger nuclease architecture for highly specific genome editing. Nat. Biotechnol. 2007;25:778-785.

Mirzabekov. DNA Sequencing by Hybridization—a Megasequencing Method and a Diagnostic Tool? Trends in Biotechnology 12(1): 27-32 (1994).

Moore, et al. Behavior of capillary valves in centrifugal microfluidic devices prepared by three-dimensional printing. Microfluidics and Nanofluidics. 2011; 10(4):877-888.

Morgan, et al. Chapter 12: Human microbiome analysis. PLoS Comput Biol. 2012;8(12):e1002808. doi: 10.1371/journal.pcbi.1002808. Epub Dec. 27, 2012.

Mouritzen et al. Single nucleotide polymorphism genotyping using locked nucleic acid (LNa). Expert Rev Mol Diagn. Jan. 2003;3(1):27-38.

Mozhanova, A.A. et al. Local elastic properties of biological materials studied by SFM (2003) XP055314108, Retrieved from the Internet: URL:http://www.ntmdt.com/data/media/files/publications/2003/08.08_a.a.mozhanova_n.i.n_english.pdf.

Muotri, et al. L1 retrotransposition in neurons is modulated by MeCP2. Nature. Nov. 18, 2010;468(7322):443-6. doi: 10.1038/nature09544.

Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.

Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.

(56) References Cited

OTHER PUBLICATIONS

Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al. Controlled Production of Monodisperse Double Emulsions by Two-Step Droplet Breakup in Microfluidic Devices. Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Pantel, et al. Detection methods of circulating tumor cells. J Thorac Dis. Oct. 2012;4(5):446-7. doi: 10.3978/j.issn.2072-1439.2012.08.15.
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al. Poly(lactic acid)-poly(ethylene glycol) Nanoparticles as new carriers for the delivery ofplasmid DNa. Journal of Controlled Release, vol. 75, pp. 211-224 (2001).
Peters, et al. Accurate whole-genome sequencing and haplotyping from 10 to 20 human cells. Nature. Jul. 11, 2012;487(7406):190-5. doi: 10.1038/Nature11236.
Picot, J. et al. A biomimetic microfluidic chip to study the circulation and mechanical retention of red blood cells in the spleen. Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Porteus MH, Baltimore D. Chimeric nucleases stimulate gene targeting in human cells. Science. 2003;300:763.
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ran, et al., Genome Engineering Using the CRISPR-Cas9 System, Nature Protocol, (2013), 8(11):2281-2308.
Richardson, et al. Novel inhibition of archaeal family-D DNA polymerase by uracil. Nucleic acids research 41.7 (2013): 4207-4218.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan. Rapid assay for mycobacterial growth and antibiotic susceptibility using gel microdrop and encapsulation. J. Clinical Microbial., 33:7 1720-1726 (1995).
Sander JD, et al. Selection-free zinc-finger-nuclease engineering by context-dependent assembly (CoDA). Nat. Methods. 2011;8:67-69.
Schirinzi et al., Combinatorial sequencing-by-hybridization: aNalysis of the NFI gene. Genet Test. 2006 Spring;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.
Schmitt. Bead-based multiplex genotyping of human papillomaviruses. J. Clinical Microbial., 44:2 504-512 (2006).
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shah. Fabrication of mono disperse thermosensitive microgels and gel capsules in micro fluidic devices. Soft Matter, 4:2303-2309 (2008).
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., DiscrimiNation between perfect and mismatched duplexes with oligonucleotide gel microchips: role of thermodynamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese JourNal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Tawfik, D.S., et al. Man-made cell-like compartments for molecular evolution. Nature Biotechnology, vol. 16, pp. 652-656 (1998).
Tayyab, S. et al. Size exclusion chromatography and size exclusion HPLC of proteins Biochem Ed, Pergamon, (1991) 19(3):149-152.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Theberge, et al. Microdropelts in microfluidics: an evolving platform for discoveries in chemsitry and biology. Angew Chem Int Ed Engl. Aug. 9, 2010;49(34):5846-68. doi: 10.1002/anie.200906653.
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1)"107-121.

(56) References Cited

OTHER PUBLICATIONS

Tubeleviciute, et al. Compartmentalized self-replication (CSR) selection of Thermococcus litoralis ShlB DNa polymerase for diminished uracil binding. Protein Eng Des Sel. Aug. 2010;23(8):589-97. doi: 10.1093/protein/gzq032. Epub May 31, 2010.
Turner, et al. Methods for genomic partitioning. Annu Rev Genomics Hum Genet. 2009;10:263-84. doi: 10.1146/annurev-genom-082908-150112. Review.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., Single nucleotide polymorphism discrimination assisted by improved base stacking hybridization using oligonucleotide microarrays. Biotechniques. 2003;35:300-08.
Weaver. Rapid clonal growth measurements at the single-cell level: gel microdroplets and flow cytometry. Biotechnology, 9:873-877 (1991).
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides. Soft lithography in biology and biochemistry. Annual Review of Biomedical Engineering, 3:335-373 (2001).
Williams et al., Amplification of complex gene libraries by emulsion PCR, Nature Methods 3(7):545-550 (2006).
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xia and Whitesides, Soft Lithography, Ann. Rev. Mat. Sci. 28:153-184 (1998).
Yamamoto, et al. Chemical modification of Ce(IV)/EDTA-base artificial restriction DNA cutter for versatile manipulation of double-stranded DNA. Nucleic Acids Research. 2007; 35(7):e53.
Zhang. Combinatorial marking of cells and organelles with reconstituted fluorescent proteins. Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang F, et al. Efficient construction of sequence-specific TAL effectors for modulating mammalian transcription. Nat. Biotechnol. 2011;29:149-153.
Zhao, J., et al. Preparation of hemoglobin-loaded Nano-sized particles with porous structure as oxygen carriers. Biomaterials, vol. 28, pp. 1414-1422 (2007).
Zheng, et al. Massively parallel digital transcriptional profiling of single cells. Nat Commun. Jan. 16, 2007;8:14049. doi: 10.1038/ncomms14049.
Zheng, X.Y. et al. Haplotyping germline and cancer genomes with high-throughput linked-read sequencing. Nature Biotech (Feb. 1, 2016) 34(3):303-311.
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypoosmolar electrofusion. Hum• Antibodies Hybridomas. Jan. 1992; 3(1 ): 14-8.
Zong, et al. Genome-wide detection of single-nucleotide and copy-number variations of a single human cell. Science. Dec. 21, 2012;338(6114):1622-6. doi: 10.1126/science.1229164.
Ahern, "Biochemical, Reagents Kits Offer Scientists Good Return on Investment" The Scientist (1995) 9(15):1-7.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Boulanger, et al, "Massively parallel haplotyping on microscopic beads for the high-throughput phase analysis of single molecules", PLoS One, vol. 7:1-10, 2012.
Brown, K., Targeted Sequencing Using Droplet-Based Microfluidics, RainDance Technologies, 2009, 1-18.
Casbon, et al, "Reflex: intramolecular barcoding of long-range PCR products for sequencing multiple pooled DNAs", Nucleic Acids Res., pp. 1-6, 2013.
Co-pending U.S. Appl. No. 15/596,754, filed May 16, 2017.
Co-pending U.S. Appl. No. 15/598,898, filed May 18, 2017.
Hiatt, et al. Parallel, tag-directed assembly of locally derived short sequence reads. Nat Methods. Feb. 2010;7(2):119-22. doi: 10.1038/nmeth.1416. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Imburgio, et al, "Studies of promoter recognition and start site selection by T7 RNA polymerase using a comprehensive collection of promoter variants", Biochemistry., 39:10419-30, 2000.
Kirkness et al. "Sequencing of isolated sperm cells for direct haplotyping of a human genome," Genome Res (2013) 23:826-832.
Kitzman et al. Haplotype-resolved genome sequencing of a Gujarati Indian individual.â€ Nat Biotechnol (2011) 29:59-63.
Konarewa, et al, "96-plex molecular barcoding for the Illumina Genome Analyzer", Methods Mol Biol., 733:279-98, 2011. cited by applicant.
Kozarewa, et al. "Amplification-free Illumina sequencing-library preparation facilitates improved mapping and assembly of GC-biased genomes", Nat Methods., 6: 291-5, 2009. cited by applicant.
Kwok, et al, "Single-molecule analysis for molecular haplotyping", Hum Mutat., 23:442-6, 2004. cited by applicant.
Laird et al, Hairpin-bisulfite PCR: Assessing epigenetic methylation patterns on complementary strands of individual DNA molecules, 2004, PNAS, 101, 204-209.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Linch, et al. Bone marrow processing and cryopreservation. Journal of Clinical Pathology; Feb. 1982, vol. 35, No. 2; pp. 186-190.
Lundin, et al, "Hierarchical molecular tagging to resolve long continuous sequences by massively parallel sequencing", Sci Rep., 3:1186, 2003.
Myllykangas et al., Targeted Sequencing Library Preparation by Genomic DNA Circularization, BMC Biotechnology, 2011, 11(122), 1-12.
Oyola, et al, "Optimizing Illumina next-generation sequencing library preparation for extremely AT-biased genomes", BMC Genomics.,13:1, 2012.
PCT/IB2010/002243, International Search Report and Written Opinion, dated Feb. 9, 2011, 13pgs.
Ramskold et al. (2012) "Full-length mRNA-Seq from single-cell levels of RNA and individual circulating tumor cells" Nature Biotechnology 30(8):777-782.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.

(56) References Cited

OTHER PUBLICATIONS

Roche. Using Multiplex Identifier (MID) Adaptors for the GS FLX Titanium Chemistry Basic Mid Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptors ForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005 UsingMultiplexIdentifierAdaptors ForTheGSFLXTitaniumChemistry-ExtendedMIDSet.pdf.
Schwartz; et al., "Capturing native long-range contiguity by in situ library construction and optical sequencing", PNAS (Nov. 2012), 109(46)18749-18754.
Stoeckius, et al. Large-scale simultaneous measurement of epitopes and transcriptomes in single cells. bioRxiv 113068; doi: https://doi.org/10.1101/113068.
Tewhey et al., Supplementary Materials, Nature Biotechnology, 2009, 27(11), 1-22.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wang; et al., "Self-Formed Adaptor PCR: a Simple and Efficient Method for Chromosome Walking", Applied and Environmental Microbiology (Aug. 2007), 73(15):5048-5051.
Wiseman, R.W. et al. "Major histocompatibility complex genotyping with massively parallel pyrosequencing" Nature Medicine (Oct. 11, 2009) 15(11):1322-1326.
Xiao, et al, "Determination of haplotypes from single DNA molecules: a method for single-molecule barcoding", Hum Mutat., 28:913-21, 2007.
Yan, Pu et al. "Rapid one-step construction of hairpin RNA" Biochem and Biophys Res Comm (Jun. 12, 2009) 383(4):464-468.
Zhang. Genomics of inherited bone marrow failure and myelodysplasia. Dissertation [online]. University of Washington. 2015 [Retrieved on May 3, 2017].
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Curcio. Improved Techniques for High-Throughput Molecular Diagnostics. PhD Thesis. 2002.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Han, X. et al. "CRISPR-Cas9 delivery to hard-to-transfect cells via membrane deformation" Science Advances (2015) 1(7): E1500454 (8 pages).
Hosokawa, et al. Massively parallel whole genome amplification for single-cell sequencing using droplet microfluidics. Scientific Reports 7, Article No. 5199 (2017).
Katsura, et al. Indirect micromanipulation of single molecules in water-in-oil emulsion. Electrophoresis. Jan. 2001;22(2):289-93.
Kenis, et al. Microfabrication Inside Capillaries Using Multiphase Laminar Flow Patterning. Science. Jul. 2, 1999;285(5424):83-5.
Lagally, et al. Single-Molecular DNA Amplification and Analysis in an Integrated Microfluidic Device. Anal Chem. Feb. 1, 2001;73(3):565-70.
Man. Monolithic Structures for Integrated Microfluidic Analysis. PhD Thesis. 2001.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Rakszewska, A. et al. "One drop at a time: toward droplet microfluidics as a versatile tool for single-cell analysis" NPG Asia Materials (2014) 6(10):e133 (12 pages).
Ramsey, J.M. "The burgeoning power of the shrinking laboratory" Nature Biotech (1999) 17:1061-1062.
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Rodrigue, S. et al. "Whole genome amplification and de novo assembly of single bacterial cells" PLoS One. Sep. 2, 2009;4(9):e6864. doi: 10.1371/journal.pone.0006864.
Schubert, et al. Microemulsifying fluorinated oils with mixtures of fluorinated and hydrogenated surfactants. Colloids and Surfaces A; Physicochemical and Engineering Aspects, 84(1994) 97-106.
Song, et al. Reactions in droplets in microfluidic channels. Angew Chem Int Ed Engl. Nov. 13, 2006;45(44):7336-56.
Thorsen, et al. Dynamic pattern formation in a vesicle-generating microfluidic device. Physical Review Letters. American Physical Society. 2001; 86(18):4163-4166.
Ward, et al. Microfluidic flow focusing: Drop size and scaling in pressure versus flow-rate-driven pumping. Electrophoresis. Oct. 2005;26(19):3716-24.
Weigl, et al. Microfluidic Diffusion-Based Separation and Detection. Science. 1999; pp. 346-347.
Zeng, et al. High-performance single cell genetic analysis using microfluidic emulsion generator arrays. Anal Chem. Apr. 15, 2010;82(8):3183-90. doi: 10.1021/ac902683t.
Xi, et al. New library construction method for single-cell genomes. PLoS One. Jul. 19, 2017;12(7):e0181163. doi: 10.1371/journal.pone.0181163. eCollection 2017.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Buchman GW, et al. Selective RNA amplification: a novel method using dUMP-containing primers and uracil DNA glycosylase. PCR Methods Appl. 1993 Aug; 3(1):28-31.
Co-pending U.S. Appl. No. 15/687,357, filed Aug. 25, 2017.
Co-pending U.S. Appl. No. 15/687,856, filed Aug. 28, 2017.
Co-pending U.S. Appl. No. 15/693,374, filed Aug. 31, 2017.
Co-pending U.S. Appl. No. 15/717,840, filed Sep. 27, 2017.
Co-pending U.S. Appl. No. 15/717,847, filed Sep. 27, 2017.
Co-pending U.S. Appl. No. 15/717,871, filed Sep. 27, 2017.
Co-pending U.S. Appl. No. 15/718,764, filed Sep. 28, 2017.
Co-pending U.S. Appl. No. 15/718,893, filed Sep. 28, 2017.
Co-pending U.S. Appl. No. 15/719,459, filed Sep. 28, 2017.
Co-pending U.S. Appl. No. 15/720,085, filed Sep. 29, 2017.
Dressman et al. Supplementary Information pp. 1-2 of article published 2003, PNAS 100(15:8817-22).
Hosono S, et al. Unbiased whole-genome amplification directly from clinical samples. Genome Res. May 2003; 13(5):954-64. Epub Apr. 14, 2003.
Kamperman, et al. Centering Single Cells in Microgels via Delayed Crosslinking Supports Long-Term 3D Culture by Preventing Cell Escape. Small. Jun. 13, 2017(22). doi: 10.1002/smll.201603711. Epub Apr. 28, 2017.
Lienemann, et al. Single cell-laden protease-sensitive microniches for long-term culture in 3D. Lab Chip. Feb. 14, 2017;17(4):727-737. doi: 10.1039/c6lc01444e.
Lo, et al. On the design of clone-based haplotyping. Genome Biol. 2013;14(9):R100.

(56) References Cited

OTHER PUBLICATIONS

Maricic T, et al. Optimization of 454 sequencing library preparation from small amounts of DNA permits sequence determination of both DNA strands. Biotechniques. Jan. 2009; 46(1):51-2, 54-7.

Perrott, Jimmy. Optimization and Improvement of Emulsion PCR for the Ion Torrent Next-Generation Sequencing Platform. (2011) Thesis.

Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.

Skerra A. Phosphorothioate primers improve the amplification of DNA sequences by DNA polymerases with proofreading activity. Nucleic Acids Res. Jul. 25, 1992; 20(14):3551-4.

Stoeckius, et al. Simultaneous epitope and transcriptome measurement in single cells. Nature methods. Jul. 31, 2017. Supplemental Materials.

\* cited by examiner

|  | 4 Cutter | 6 Cutter |
|---|---|---|
| Pair 1 | MspI C/CGG | NarI GG/CGCC |
| Pair 2 | BfaI C/TAG | NdeI CA/TATG |
| Pair 3 | HinP1I G/CGC | ClaI AT/CGAT |
| Pair 4 | MseI T/TAA | NdeI CA/TATG |
| Pair 5 | CviQI G/TAC | NdeI CA/TATG |
| Pair 6 | TaqαI T/CGA | AclI AA/CGTT |

*Fig. 7A*

|  | 4 Cutter | 6 Cutter |
|---|---|---|
| Pair 1 | RsaI GT/AC | PmeI GTTT/AAAC |
| Pair 2 | AluI AG/CT | EcoRV GAT/ATC |
| Pair 3 | BstUI CG/CG | PmeI GTTT/AAAC |
| Pair 4 | DpnI GA/TC | StuI AGG/CCT |
| Pair 5 | HaeIII GG/CC | PmeI GTTT/AAAC |
| Pair 6 | HpyCH4V TG/CA | SfoI GGC/GCC |

*Fig. 7B*

SEQUENCE LISTING

<160> NUMBER OF SEQ ID NOS: 13

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

```
<220> FEATURE:
<221> NAME/KEY: modified_base
<222> LOCATION: (5)..(9)
<223> OTHER INFORMATION: a, c, t, g, unknown or other

<400> SEQUENCE: 1
ggccnnnnng gcc                                                          13

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 2
caannnnngt gg                                                           12

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(10)
<223> OTHER INFORMATION: a, c, t, g, unknown or other

<400> SEQUENCE: 3
gaannnnnnn ttgg                                                         14

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 4
gaacnnnnnn tcc                                                          13

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 5
gaagnnnnnn tac                                                          13
```

```
<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 6
gaacnnnnnc tc                                                             12

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 7
gaacnnnnnn tac                                                            13

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atcctttaag c                                                              11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggatcaagct a                                                              11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aaattccggc a                                                              11

<210> SEQ ID NO 11
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (10)..(19)
<223> OTHER INFORMATION: a, c, t, g, unknown or other
<220> FEATURE:
<221> NAME/KEY: modified_base
<222> LOCATION: (24)..(28)
<223> OTHER INFORMATION: a, c, t, g, unknown or other

<400> SEQUENCE: 11
nnnnnccggn nnnnnnnnnc cggnnnnn                                         28

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (12)..(16)
<223> OTHER INFORMATION: a, c, t, g, unknown or other

<400> SEQUENCE: 12
nnnnnggcgc cnnnnn                                                      16

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (11)..(20)
<223> OTHER INFORMATION: a, c, t, g, unknown or other
<220> FEATURE:
<221> NAME/KEY: modified_base
<222> LOCATION: (26)..(30)
<223> OTHER INFORMATION: a, c, t, g, unknown or other

<400> SEQUENCE: 13
nnnnnggcgg nnnnnnnnnn ccgccnnnnn                                       30
```

METHODS AND SYSTEMS FOR PROCESSING POLYNUCLEOTIDES

CROSS-REFERENCE

This application is a continuation of U.S. patent application Ser. No. 15/376,582, filed Dec. 12, 2016, which is a continuation-in-part of U.S. patent application Ser. No. 14/104,650, filed on Dec. 12, 2013, now U.S. Pat. No. 9,567,631, which claims priority to U.S. Provisional Application No. 61/737,374, filed on Dec. 14, 2012; U.S. patent application Ser. No. 15/376,582 is also a continuation-in-part of U.S. patent application Ser. No. 14/250,701, filed on Apr. 11, 2014, which is a continuation of U.S. patent application Ser. No. 14/175,973, filed on Feb. 7, 2014, now U.S. Pat. No. 9,388,465, which claims priority to U.S. Provisional Application No. 61/844,804, filed on Jul. 10, 2013, U.S. Provisional Application No. 61/840,403, filed on Jun. 27, 2013, U.S. Provisional Application No. 61/800,223, filed on Mar. 15, 2013, and U.S. Provisional Application No. 61/762,435, filed on Feb. 8, 2013, each of which is entirely incorporated herein by reference for all purposes.

SEQUENCE LISTING

The instant application contains a Sequence Listing which has been submitted electronically in ASCII format and is hereby incorporated by reference in its entirety. Said ASCII copy, created on Jan. 6, 2017, is named 43487703501SL.txt and is 5 kilobytes in size.

BACKGROUND

The processing of polynucleotides and polynucleotide fragments is a critical aspect of a wide variety of technologies, including polynucleotide sequencing. Polynucleotide sequencing continues to find more widespread use in medical applications such as genetic screening and genotyping of tumors. Many polynucleotide sequencing methods rely on sample processing techniques solely utilizing random fragmentation of polynucleotides. Such random, uncontrolled fragmentation can introduce several problems in downstream processing. For example, these methods may produce fragments with large variation in length, including a large number or fraction of sequences that are too long to be sequenced accurately. This results in a loss of sequence information. Current methods of processing may also damage polynucleotides, resulting in incorrect sequence information, and/or the loss of sequence information. These, and other, problems may be significantly amplified by relatively minor operator variability. Thus, there is a significant need for improved methods that provide better control over all aspects of polynucleotide fragmentation and processing. In particular, there is need for polynucleotide processing methods that consistently provide fragments of appropriate size and composition for any downstream application, including sequencing.

SUMMARY

I. Non-Overlapping Fragmentation

This disclosure provides methods, compositions, systems, and devices for processing polynucleotides. In one example, a method provided herein comprises: (a) providing a target polynucleotide; (b) fragmenting said target polynucleotide to generate a plurality of non-overlapping first polynucleotide fragments; (c) partitioning said first polynucleotide fragments to generate partitioned first polynucleotide fragments, wherein at least one partition of said partitioned first polynucleotide fragments comprises a first polynucleotide fragment with a unique sequence within said at least one partition; and (d) fragmenting said partitioned first polynucleotide fragments, to generate a plurality of non-overlapping second polynucleotide fragments.

In some of the methods provided in this disclosure, a third and fourth set of polynucleotide fragments are generated by performing the method described above and additionally performing a method comprising: (a) fragmenting said target polynucleotide to generate a plurality of non-overlapping third polynucleotide fragments; (b) partitioning said third polynucleotide fragments to generate partitioned third polynucleotide fragments, wherein at least one partition of said partitioned third polynucleotide fragments comprises a third polynucleotide fragment with a unique sequence within said at least one partition; and (c) fragmenting said partitioned third polynucleotide fragments to generate a plurality of non-overlapping fourth polynucleotide fragments.

The third polynucleotide fragments may overlap with the first polynucleotide fragments. The fourth polynucleotide fragments may overlap with the second polynucleotide fragments.

The target polynucleotide may be, for example, DNA, RNA, cDNA, or any other polynucleotide.

In some cases, at least one of the first, second, third, and fourth polynucleotide fragments are generated by an enzyme. The enzyme may be a restriction enzyme. The restriction enzyme used to generate the first polynucleotide fragments may be different from the restriction enzyme used to generate the third polynucleotide fragments. The restriction enzyme used to generate the second polynucleotide fragments may be different from the restriction enzyme used to generate the fourth polynucleotide fragments. The restriction enzymes may have a recognition site of at least about six nucleotides in length.

The fragments can be of a variety of lengths. For example, the first and/or third polynucleotide fragments may have a median length of least about 10,000 nucleotides. The second or fourth polynucleotide fragments may have a median length of less than about 200 nucleotides.

The fragments can be attached to barcodes. For example, the second polynucleotide fragments and/or the fourth polynucleotide fragments may be attached to barcodes, to generate barcoded second and/or fourth polynucleotide fragments. The barcodes may be polynucleotide barcodes. The attachment of the barcodes to the polynucleotide fragments may be performed using an enzyme. The enzyme may be a ligase. The barcoded fragments may be pooled. Unpooled or pooled barcoded fragments may be sequenced.

In some cases, one or more steps of the methods described in this disclosure may be performed within a device. The device may comprise at least one well. The well may be a microwell. Any of the partitioning steps described in this disclosure may be performed by dispensing into a microwell.

The microwell (or well) may comprise reagents. These reagents may be any reagent, including, for example, barcodes, enzymes, adapters, and combinations thereof. The reagents may be physically separated from a polynucleotide sample placed in the microwell. This physical separation may be accomplished by containing the reagents within a microcapsule that is placed within a microwell. The physical separation may also be accomplished by dispensing the reagents in the microwell and overlaying the reagents with a layer that is, for example, dissolvable, meltable, or permeable prior to introducing the polynucleotide sample into the microwell. This layer may be, for example, an oil, wax, membrane, or the like. The microwell may be sealed at any point, for example after addition of the microcapsule, after addition of the reagents, or after addition of either of these components plus a polynucleotide sample.

Partitioning may also be performed by a variety of other means, including through the use of fluid flow in microfluidic channels, by emulsification, using spotted arrays, by surface acoustic waves, and by piezoelectric droplet generation.

Additional methods of fragmenting nucleic acids that are compatible with the methods provided herein include mechanical disruption, sonication, chemical fragmentation, treatment with UV light, and heating, and combinations thereof. These methods may be used to fragment, for example, the partitioned first or third polynucleotide fragments described above.

Partitioning may be done at any time. For example, the first polynucleotide fragments and/or the third polynucleotide fragments may each be further partitioned into two or more partitions before further processing.

Pseudo-Random Fragmentation

This disclosure provides methods for pseudo-random fragmentation of polynucleotides. In some cases, such methods comprise: (a) providing a target polynucleotide; (b) fragmenting said target polynucleotide to generate a plurality of first polynucleotide fragments; (c) partitioning said first polynucleotide fragments to generate partitioned first polynucleotide fragments, such that at least one partition comprises a first polynucleotide fragment with a unique sequence within said at least one partition; and (d) fragmenting said partitioned first polynucleotide fragments with at least one restriction enzyme in at least one partition, to generate a plurality of second polynucleotide fragments, wherein said partitioned first polynucleotide fragment is fragmented with at least two restriction enzymes across all partitions.

In some cases, at least two restriction enzymes are disposed within the same partition. In some cases, at least two restriction enzymes are disposed across a plurality of different partitions.

The pseudo-random fragmentation methods can be performed in order to yield fragments of a certain size. In some cases, at least about 50% of the nucleotides within a target polynucleotide are within about 100 nucleotides of a restriction site of a restriction enzyme used to perform pseudo-random fragmentation. In some cases, at most about 25% of the nucleotides within a target polynucleotide are within about 50 nucleotides of a restriction site of a restriction enzyme used to perform pseudo-random fragmentation. In some cases, at most about 10% of the nucleotides within a target polynucleotide are more than about 200 nucleotides from a restriction site a restriction enzyme used to perform pseudo-random fragmentation.

A polynucleotide may be treated with two or more restriction enzymes concurrently or sequentially.

The pseudo-randomly fragmented polynucleotides may be attached to barcodes, to generate barcoded polynucleotide fragments. The barcoded polynucleotides may be pooled and sequenced.

The number of partitions holding the partitioned first polynucleotide fragments may be at least about 1,000 partitions. The volume of these partitions may be less than about 500 nanoliters.

Each enzyme may occupy an equivalent number of partitions, or each enzyme may occupy a different number of partitions.

III. Restriction Enzyme-Mediated Recycling

This disclosure provides methods for recycling certain unwanted reaction side products back into starting materials that can be used to generate a desired product. In some cases, these methods comprise: (a) providing a first polynucleotide, a second polynucleotide, a first restriction enzyme, and a second restriction enzyme, wherein said first polynucleotide comprises a target polynucleotide or a fragment thereof; and (b) attaching said first polynucleotide to said second polynucleotide, to generate a polynucleotide product, wherein said first restriction enzyme cuts a polynucleotide generated by attachment of said first polynucleotide to itself, said second restriction enzyme cuts a polynucleotide generated by attachment of said second polynucleotide to itself, and neither said first restriction enzyme nor said second restriction enzyme cuts said polynucleotide product.

The first polynucleotide may be generated in the same reaction volume as the polynucleotide product, or in a different reaction volume. The target polynucleotide may be, for example, a fragment of genomic DNA.

The second polynucleotide may be generated in the same reaction volume as the polynucleotide product, or in a different reaction volume. The second polynucleotide may be, for example, a barcode or an adapter.

The first restriction enzyme may have a recognition site of at most about four nucleotides in length. The second restriction enzyme may have a recognition site of at least about six nucleotides in length. The first restriction enzyme may have a recognition site of about four nucleotides in length. The second restriction enzyme may have a recognition site of at least about five nucleotides in length.

The first and second restriction enzymes may generate ligation compatible ends. These ends may have single-stranded overhangs (i.e., "sticky ends") or be blunt. The sticky ends may match in sequence and orientation, to allow ligation. The attachment step may be performed by ligation.

The sequence 5' to the ligation compatible end generated by the first restriction enzyme may be different from the sequence 5' to the ligation compatible end generated by the second restriction enzyme. This will ensure that the desired product cannot be re-cut by either restriction enzyme.

The sequence 3' to the ligation compatible end generated by the first restriction enzyme may be different from the sequence 3' to the ligation compatible end generated by the second restriction enzyme. This will ensure that the desired product cannot be re-cut by either restriction enzyme. Given the criteria provided throughout this specification, one of ordinary skill in the art will recognize that many pairs of enzymes are suitable for use with this method.

The recycling may provide increased yield of the desired product, for example at least about 75% (w/w).

Also provided by this disclosure is a polynucleotide fragment generated by any of the methods provided herein, devices for performing the methods provided herein, and systems for performing the methods provided herein.

The methods provided in this disclosure (and portions thereof) may also be used with each other. For example, the non-overlapping fragmentation methods may be used alone and/or with the pseudo-random fragmentation methods and/or with the restriction enzyme-mediated recycling methods. Likewise, the pseudo-random fragmentation methods may be used alone and/or with the non-overlapping fragmentation methods and/or with the restriction enzyme-mediated recycling methods. Similarly, the restriction enzyme-mediated recycling methods may be used alone and/or with the non-overlapping fragmentation methods and/or with the pseudo-random fragmentation methods.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of methods, compositions, systems, and devices of this disclosure are set forth with particularity in the appended claims. A better understanding of the features and advantages of this disclosure will be obtained by reference to the following detailed description that sets forth illustrative embodiments, in which the principles of the methods, compositions, systems, and devices of this disclosure are utilized, and the accompanying drawings of which:

FIG. 2 discloses SEQ ID NOS 8-10, respectively, in order of appearance.

FIG. 6 discloses SEQ ID NOS 11 and 11-13, respectively, in order of appearance.

FIG. 7A shows exemplary 4Mer cutter and 6Mer cutter pairs generating sticky ends.

FIG. 7B shows exemplary 4Mer cutter and 6Mer cutter pairs generating blunt ends.

DETAILED DESCRIPTION

Figure 1:
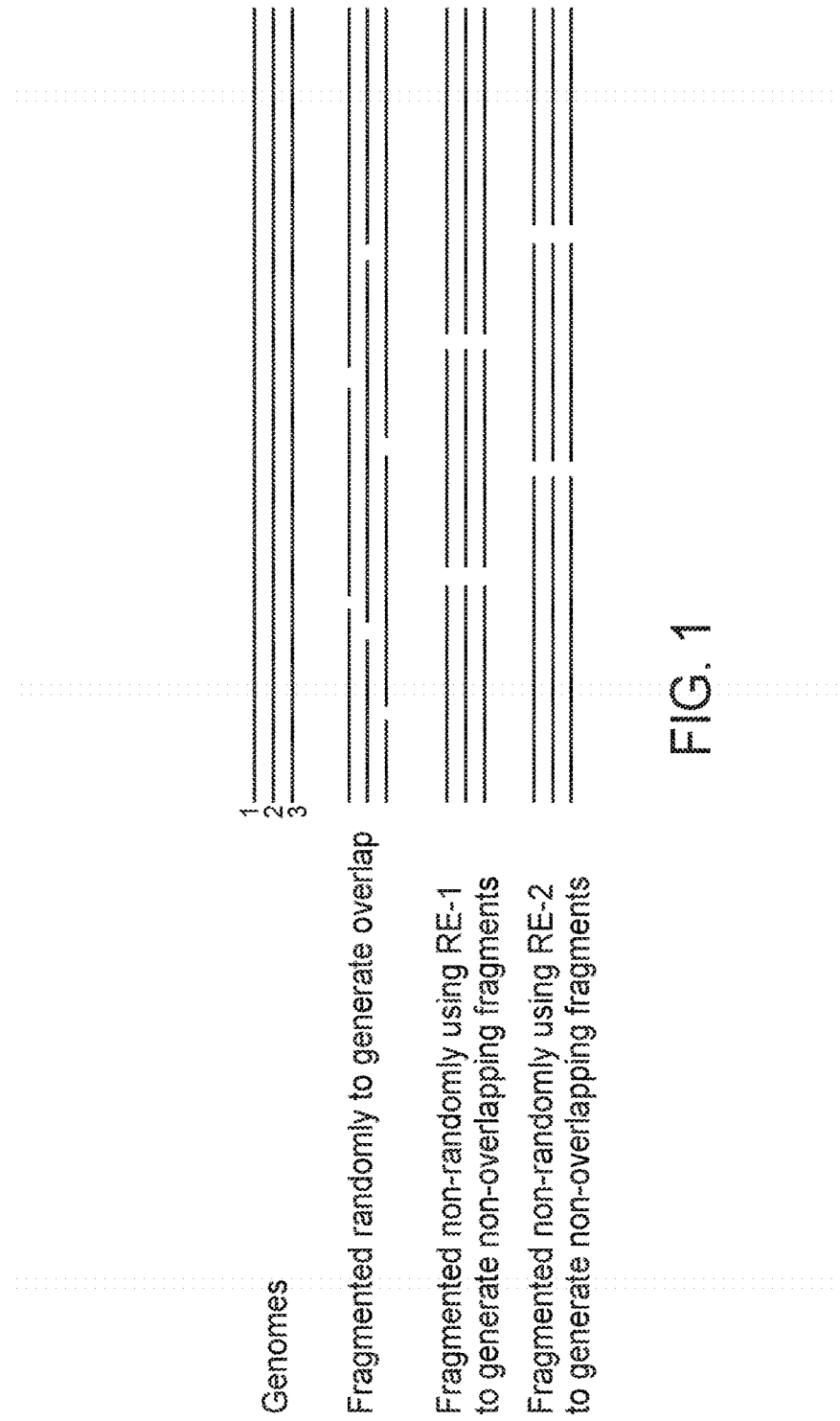
FIG. 1 is a schematic representation of overlapping and non-overlapping deoxyribonucleic acid (DNA) fragments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

This disclosure provides methods, compositions, systems, and devices for processing polynucleotides. Applications include processing polynucleotides for polynucleotide sequencing. Polynucleotides sequencing includes the sequencing of whole genomes, detection of specific sequences such as single nucleotide polymorphisms (SNPs) and other mutations, detection of nucleic acid (e.g., deoxyribonucleic acid) insertions, and detection of nucleic acid deletions.

Utilization of the methods, compositions, systems, and devices described herein may incorporate, unless otherwise indicated, conventional techniques of organic chemistry, polymer technology, microfluidics, molecular biology and recombinant techniques, cell biology, biochemistry, and immunology. Such conventional techniques include microwell construction, microfluidic device construction, polymer chemistry, restriction digestion, ligation, cloning, polynucleotide sequencing, and polynucleotide sequence assembly. Specific, non-limiting, illustrations of suitable techniques are described throughout this disclosure. However, equivalent procedures may also be utilized. Descriptions of certain techniques may be found in standard laboratory manuals, such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), and "Oligonucleotide Synthesis: A Practical Approach" 1984, IRL Press London, all of which are herein incorporated in their entirety by reference for all purposes.

I. Definitions

The terminology used herein is for the purpose of describing particular embodiments only and is not intended to be limiting.

As used herein, the singular forms "a," "an," and "the" are intended to include the plural forms as well, unless the context clearly indicates otherwise. Furthermore, to the extent that the terms "including", "includes", "having", "has", "with", "such as", or variants thereof, are used in either the specification and/or the claims, such terms are not limiting and are intended to be inclusive in a manner similar to the term "comprising".

The term "about," as used herein, generally refers to a range that is 15% greater than or less than a stated numerical value within the context of the particular usage. For example, "about 10" would include a range from 8.5 to 11.5.

The term "barcode", as used herein, generally refers to a label that may be attached to a polynucleotide, or any variant thereof, to convey information about the polynucleotide. For example, a barcode may be a polynucleotide sequence attached to all fragments of a target polynucleotide contained within a particular partition. This barcode may then be sequenced with the fragments of the target polynucleotide. The presence of the same barcode on multiple sequences may provide information about the origin of the sequence. For example, a barcode may indicate that the sequence came from a particular partition and/or a proximal region of a genome. This may be particularly useful when several partitions are pooled before sequencing.

The term "bp," as used herein, generally refers to an abbreviation for "base pairs".

The term "Mer," as used herein to refer to restriction enzymes, generally refers to the number of nucleotides in one strand of a restriction enzyme's recognition site. For example, the enzyme CviQI has a recognition site of GTAC (4 nucleotides on one strand) and is thus referred to as a "4Mer cutter." The enzyme StuI has a recognition site of AGGCCT (6 nucleotides on one strand) and is thus referred to as a "6Mer cutter."

The term "microwell," as used herein, generally refers to a well with a volume of less than 1 mL. Microwells may be made in various volumes, depending on the application. For example, microwells may be made in a size appropriate to accommodate any of the partition volumes described herein.

The terms "non-overlapping" and "overlapping," as used to refer to polynucleotide fragments, generally refer to a collection of polynucleotide fragments without overlapping sequence or with overlapping sequence, respectively. By way of illustration, consider a hypothetical partition containing three copies of a genome (FIG. 1, top set of sequences). This genome may be fragmented randomly (e.g., by shearing in a pipette) or non-randomly (e.g., by digesting with a rare cutter). Fragmenting randomly produces overlapping sequences (second set of sequences from top in FIG. 1, "Fragmented randomly to generate overlap"), because each copy of the genome is cut at different positions. After sequencing of the fragments (which provides "sequence contigs"), this overlap may be used to determine the linear order of the fragments, thereby enabling assembly of the entire genomic sequence. By contrast, fragmenting by digesting with a rare cutter produces non-overlapping fragments, because each copy of the (same) genome is cut at the same position (third set of sequences from the top in FIG. 1, "Fragmented non-randomly using RE-1 to generate non-overlapping fragments"). After sequencing these fragments, it may be difficult to deduce their linear order due to the lack of overlap between the fragments. However, as described in this disclosure, the linear order may be determined by, for example, fragmenting the genome using a different technique. The fourth set of sequences from the top of FIG. 1 demonstrates the use of a second rare-cutter enzyme to generate a second set of non-overlapping fragments ("Fragmented non-randomly using RE-2 to generate non-overlapping fragments"). Because two different enzymes, for example, are used to generate the two sets of non-overlapping fragments, there is overlap between the fragments generated with the first rare-cutter enzyme (RE-1) and the fragments generated with the second rare-cutter enzyme (RE-2). This overlap may then be used to assemble the linear order of the sequences, and therefore the sequence of the entire genome.

The term "partition," as used herein, may be a verb or a noun. When used as a verb (e.g., "partitioning"), the term refers to the fractionation of a substance (e.g., a polynucleotide) between vessels that can be used to sequester one fraction from another. Such vessels are referred to using the noun "partition." Partitioning may be performed, for example, using microfluidics, dilution, dispensing, and the like. A partition may be, for example, a well, a microwell, a droplet, a test tube, a spot, or any other means of sequestering one fraction of a sample from another. In the methods and systems described herein, polynucleotides are often partitioned into microwells.

The terms "polynucleotide" or "nucleic acid," as used herein, are used herein to refer to biological molecules comprising a plurality of nucleotides. Exemplary polynucleotides include deoxyribonucleic acids, ribonucleic acids, and synthetic analogues thereof, including peptide nucleic acids.

The term "rare-cutter enzyme," as used herein, generally refers to an enzyme with a recognition site that occurs only rarely in a genome. The size of restriction fragments generated by cutting a hypothetical random genome with a restriction enzyme may be approximated by $4^N$, where N is the number of nucleotides in the recognition site of the enzyme. For example, an enzyme with a recognition site consisting of 7 nucleotides would cut a genome once every $4^7$ bp, producing fragments of about 16,384 bp. Generally rare-cutter enzymes have recognition sites comprising 6 or more nucleotides. For example, a rare cutter enzyme may have a recognition site comprising or consisting of 6, 7, 8, 9, 10, 11, 12, 13, 14, or 15 nucleotides. Examples of rare-cutter enzymes include NotI (GCGGCCGC), XmaIII (CGGCCG), SstII (CCGCGG), SalI (GTCGAC), NruI (TCGCGA), NheI (GCTAGC), Nb.BbvCI (CCTCAGC), BbvCI (CCTCAGC), AscI (GGCGCGCC), AsiSI (GCGATCGC), FseI (GGCCGGCC), PacI (TTAATTAA), PmeI (GTTTAAAC), SbfI (CCTGCAGG), SgrAI (CRCCGGYG), SwaI (ATTTAAAT), BspQI (GCTCTTC), SapO (GCTCTTC), SfiI (GGCCNNNNNGGCC (SEQ ID NO: 1)), CspCI (CAANNNNNGTGG (SEQ ID NO: 2)), AbsI (CCTCGAGG), CciNI (GCGGCCGC), FspAI (RTGCGCAY), MauBI (CGCGCGCG), MreI (CGCCGGCG), MssI (GTTTAAAC), PalAI (GGCGCGCC), Rgal (GCGATCGC), RigI (GGCCGGCC), SdaI (CCTGCAGG), SfaAI (GCGATCGC), SgfI (GCGATCGC), SgrDI (CGTCGACG), SgsI (GGCGCGCC), SmiI (ATTTAAAT), SrfI (GCCCGGGC), Sse2321 (CGCCGGCG), Sse83871 (CCTGCAGG), LguI (GCTCTTC), PciSI (GCTCTTC), AarI (CACCTGC), AjuI (GAANNNNNNNTTGG (SEQ ID NO: 3)), AloI (GAACNNNNNNTCC (SEQ ID NO: 4)), Bad (GAAGNNNNNNTAC (SEQ ID NO: 4)), PpiI (GAACNNNNNCTC (SEQ ID NO: 6)), Psd (GAACNNNNNNTAC (SEQ ID NO: 7)), and others.

The term "target polynucleotide," as used herein, generally refers to a polynucleotide to be processed. For example, if a user intends to process genomic DNA into fragments that may be sequenced, the genomic DNA would be the target polynucleotide. If a user intends to process fragments of a polynucleotide, then the fragments of the polynucleotide may be the target polynucleotide.

II. Non-Overlapping Fragmentation

This disclosure provides methods, compositions, systems, and devices for the generation of non-overlapping polynucleotide fragments. These fragments may be useful for downstream analyses such as DNA sequencing. For example, with reference to FIG. 2, a target polynucleotide 101, such as genomic DNA, may be fragmented to generate a plurality of non-overlapping first polynucleotide fragments 102. This fragmentation may be performed, for example, by digesting the target polynucleotide with a rare-cutter enzyme (e.g., rare-cutter enzyme 1), or an artificial restriction DNA cutter (ARCUT; Yamamoto et al., *Nucleic Acids Res.*, 2007, 35(7), e53). The first polynucleotide fragments may then be partitioned, such that at least one partition 103 comprises a first polynucleotide fragment with a unique sequence within that partition and, optionally, an additional first polynucleotide fragment with a different sequence 104. The partitioned first polynucleotide fragments may then be further fragmented to produce a plurality of non-overlapping second polynucleotide fragments 105. This fragmentation may be performed, for example, by enzymatic digestion, exposure to ultraviolet (UV) light, ultrasonication, and/or mechanical agitation. The second polynucleotide fragments may be of a size that is appropriate for DNA sequencing, i.e., a size that enables a DNA sequencer to obtain accurate sequence data for the entire fragment.

In order to facilitate DNA sequence assembly, the second fragments may be attached to a barcode, which may be attached to all of the second fragments disposed in a particular partition. The barcode may be, for example, a DNA barcode. With continued reference to FIG. 2, after attachment of the barcode, the barcoded fragments may be pooled into a partition comprising pooled, barcoded sequences 106. Three barcodes are depicted as [1], [2], and [3] in 106. The pooled fragments may be sequenced.

Certain methods of genome sequence assembly rely on the presence of overlapping fragments in order to generate higher order sequence data (e.g., whole genome sequences) from sequenced fragments. The methods, compositions, systems, and devices provided herein may also be used to provide overlapping fragments. For example, with continued reference to FIG. 2, fragments overlapping with the first and second fragments described above may be generated by generating a plurality of non-overlapping third polynucleotide fragments from the target polynucleotide 107. The third polynucleotide fragments may be generated, for example, by digesting the target polynucleotide 101 with a rare-cutter enzyme (e.g., rare-cutter enzyme 2; or ARCUT) that is different from the rare-cutter enzyme used to generate the first polynucleotide fragments. If rare-cutter enzymes 1 and 2 are chosen to cut the target polynucleotide sequence at different positions, the third polynucleotide fragments and the first polynucleotide fragments will overlap. The third polynucleotide fragments may then be processed as described above for the first polynucleotide fragments.

Specifically, the third polynucleotide fragments may be partitioned such that at least one partition 108 comprises a third polynucleotide fragment with a unique sequence within that partition and, optionally, an additional third polynucleotide fragment with a different sequence 109. These partitioned fragments may then be further fragmented to produce a plurality of non-overlapping fourth polynucleotide fragments 110. The fourth polynucleotides fragments and the second polynucleotide fragments may overlap. As for the second polynucleotide fragments, the fourth polynucleotide fragments may be generated by, for example, enzymatic digestion, exposure to ultraviolet (UV) light, ultrasonication, and/or mechanical agitation. The fourth fragments may be of a size that is appropriate for DNA sequencing, i.e., a size that enables a DNA sequencer to obtain accurate sequence data for the entire fragment.

In order to facilitate DNA sequencing, the fourth fragments may be attached to a barcode, which may be attached to all of the fourth fragments disposed in a particular partition. The barcode may be, for example, a DNA barcode. After attachment of the barcode, the barcoded fragments may be pooled, into a partition comprising pooled, barcoded, sequences 111. Three barcodes are depicted as [4], [5], and [6] in 111. The pooled fragments may be sequenced. The overlap between the sequences of the second fragments and the fourth fragments may be used to assemble higher order sequences, such whole genome sequences.

The steps described above may be performed using a variety of techniques. For example, certain steps of the methods may be performed in a device comprising microwell chambers (microwells), for example a microfluidic device. These microwells may be connected to each other, or to a source of reagents, by channels. The first and third fragments may be generated outside of the device and then introduced into the device (or separate devices) for further processing. Partitioning of the first and third fragments may accomplished using fluidic techniques. Generation of the second and fourth fragments may then occur within the microwells of the device or devices. These microwells may contain reagents for barcoding of the second and fourth fragments, such as DNA barcodes, ligase, adapter sequences, and the like. Microwells may feed or be directed into a common outlet, so that barcoded fragments may be pooled or otherwise collected into one or more aliquots which may then be sequenced.

In another example, the entire process could be performed within a single device. For example, a device could be split into two sections. A first section may comprise a partition comprising rare-cutter enzyme 1 (generating first polynucleotide fragments) and a second section may comprise a partition comprising rare-cutter enzyme 2 (generating third polynucleotide fragments). An aliquot of the target polynucleotide sequence may be placed into each of these partitions. Following digestion, the enzyme may be inactivated and the samples may be partitioned, fragmented, barcoded, pooled, and sequenced as described above. For convenience, this example has been described using rare-cutter enzymes as the means of generating the first and third fragments. However, this is not intended to be limiting, here or anywhere else in this disclosure. One of ordinary skill in the art will readily recognize that other means of generating non-overlapping, or predominantly non-overlapping, fragments would be just as suitable as the use of rare-cutter enzymes.

III. Pseudo-Random Fragmentation

This disclosure also provides methods, compositions, systems, and devices for fragmenting polynucleotides in a pseudo-random manner. This may be performed by treating partitioned polynucleotides with more than one restriction enzyme. For example, polynucleotides partitioned into microwells may be treated with combinations of restriction enzymes. Within each partition containing a particular combination of enzymes, the cutting is defined and predictable. However, across all of the partitions (through the use of multiple combinations of restriction enzymes in different partitions), the polynucleotide fragments generated approximate those obtained from methods of random fragmentation. However, these polynucleotide fragments are generated in a much more controlled manner than random fragments generated by methods known in the art (e.g., shearing). The partitioned, pseudo-randomly fragmented polynucleotides may be barcoded, as described throughout this disclosure, pooled, and sequenced. The pseudo-random fragmentation methods may be used with the non-overlapping fragmentation methods described herein, or with any other method described herein such as the high yield adapter/barcode attachment method. Pseudo-random fragmentation may occur by exposing a polynucleotide to multiple enzymes simultaneously, sequentially, or simultaneously and sequentially.

Thus, this disclosure provides methods and systems for processing polynucleotides comprising generating pseudo-random fragments of said polynucleotides. These pseudo random fragments are generated by treating a polynucleotide with more than one restriction enzyme. For example, a polynucleotide may be treated with about 2, 3, 4, 5, 6, 7, 8, 9, 10, 11, 12, 13, 14, 15, 16, 17, 18, 19, 20, 25, 30, 35, 45, 45, 50, or more restriction enzymes. A polynucleotide may be treated with at least 2, 3, 4, 5, 6, 7, 8, 9, 10, 11, 12, 13, 14, 15, 16, 17, 18, 19, 20, 25, 30, 35, 45, 45, 50, or more restriction enzymes. A polynucleotide may be treated with at least 2 but fewer than 4, 5, 6, 7, 8, 9, 10, 11, 12, 13, 14, 15, 16, 17, 18, 19, 20, 25, 30, 35, 45, 45, or 50 restriction enzymes. A polynucleotide may be treated with about 2-4, 4-6, 6-8, 8-10, 10-12, 12-14, 14-16, 16-18, 18-20, 20-25, 25-30, 35-40, 40-45, or 45-50 restriction enzymes.

The restriction enzymes may be chosen in order to maximize the number or fraction of fragments that will provide accurate sequencing data, based on the size of the fragments generated by the pseudo-random fragmentation. For present day sequencing technology, accuracy degrades beyond a read length of about 100 nucleotides. Therefore, fragments of about 200 or fewer nucleotides generally provide the most accurate sequence data since they can be sequenced from either end. Fragments below about 50 nucleotides are generally less desirable because, although the produce accurate sequencing data, they underutilize the read length capacity of current sequencing instruments which are capable of 150 to 200 base reads. Fragments of about 200 to about 400 nucleotides may be sequenced with systematic errors introduced as the read length increases beyond the initial 100 bases from each end. Sequence information from fragments greater than about 400 nucleotides is typically completely lost for those bases greater than 200 bases from either end. One of skill in the art will recognize that sequencing technology is constantly advancing and that the ability to obtain accurate sequence information from longer fragments is also constantly improving. Thus, the pseudo-random fragmentation methods presented herein may be used to produce optimal fragment lengths for any sequencing method.

In some cases, fragments may be defined by the distance of their component nucleotides from a restriction site (measured in nucleotides). For example, each nucleotide within a polynucleotide fragment generated by the pseudo-random fragmentation method may be less than about 10, 50, 75, 100, 125, 150, 175, 200, 250, 300, 350, 400, 550, 600, 1000, 5000, 10000, or 100000 nucleotides from the restriction site of an enzyme to which the polynucleotide is exposed. Each nucleotide within a polynucleotide fragment may be about 10, 50, 75, 100, 125, 150, 175, 200, 250, 300, 350, 400, 550, 600, 1000, 5000, 10000, or 100000 nucleotides from the restriction site of an enzyme to which the polynucleotide is exposed. Each nucleotide within a polynucleotide fragment may be at least about 10, 50, 75, 100, 125, 150, 175, 200, 250, 300, 350, 400, 550, 600, 1000, 5000, 10000, or 100000 nucleotides from the restriction site of an enzyme to which the polynucleotide is exposed.

In some cases, at least about 5%, 10%, 15%, 20%, 25%, 30%, 35%, 40%, 45%, 50%, 55%, 60%, 65%, 70%, 75%, 80%, 85%, 90%, or 95%, of the nucleotides comprising a target polynucleotide sequence are within about 10, 50, 75, 100, 125, 150, 175, 200, 250, 300, 350, 400, 550, 600, 1000, 5000, 10000, or 100000 nucleotides from the restriction site of an enzyme to which the polynucleotide is exposed. All combinations of these percentages and polynucleotide lengths are contemplated.

In some cases, at less than about 1%, 5%, 10%, 25%, 30%, 35%, 40%, 45%, or 50% of the nucleotides comprising a target polynucleotide sequence are within about 1, 5, 10, 50, 200, 250, 300, 350, 400, 550, 600, 1000, 5000, 10000, or 100000 nucleotides from the restriction site of an enzyme to which the polynucleotide is exposed. All combinations of these percentages and polynucleotide lengths are contemplated.

The pseudo-random fragmentation methods may be used to obtain fragments of about 10 to 50 nucleotides, 46 to 210 nucleotides, 50 to 250 nucleotides, 250 to 400 nucleotides, 400 to 550 nucleotides, 550 to 700 nucleotides, 700 to 1000 nucleotides, 1000 to 1300 nucleotides, 1300 to 1600 nucleotides, 1600 to 1900 nucleotides, 1900 to 2200 nucleotides, or 2200 to 3000 nucleotides. The pseudo-random fragmentation methods may be used to obtain fragments with a mean or median of about 40 nucleotides, 60 nucleotides, 80 nucleotides, 100 nucleotides, 120 nucleotides, 130 nucleotides, 140 nucleotides, 160 nucleotides, 180 nucleotides, 200 nucleotides, 250 nucleotides, 300 nucleotides, 400 nucleotides, 500 nucleotides, 600 nucleotides, 700 nucleotides, 800 nucleotides, 900 nucleotides, 1000 nucleotides, 1200 nucleotides, 1400 nucleotides, 1600 nucleotides, 1800 nucleotides, 2000 nucleotides, 2500 nucleotides, 3000 nucleotides, or more. The pseudo-random fragmentation methods may be used to obtain fragments with a mean or median of at least about 40 nucleotides, 60 nucleotides, 80 nucleotides, 100 nucleotides, 120 nucleotides, 130 nucleotides, 140 nucleotides, 160 nucleotides, 180 nucleotides, 200 nucleotides, 250 nucleotides, 300 nucleotides, 400 nucleotides, 500 nucleotides, 600 nucleotides, 700 nucleotides, 800 nucleotides, 900 nucleotides, 1000 nucleotides, 1200 nucleotides, 1400 nucleotides, 1600 nucleotides, 1800 nucleotides, 2000 nucleotides, 2500 nucleotides, 3000 nucleotides, or more. The pseudo-random fragmentation methods may be used to obtain fragments with a mean or median of less than about 40 nucleotides, 60 nucleotides, 80 nucleotides, 100 nucleotides, 120 nucleotides, 130 nucleotides, 140 nucleotides, 160 nucleotides, 180 nucleotides, 200 nucleotides, 250 nucleotides, 300 nucleotides, 400 nucleotides, 500 nucleotides, 600 nucleotides, 700 nucleotides, 800 nucleotides, 900 nucleotides, 1000 nucleotides, 1200 nucleotides, 1400 nucleotides, 1600 nucleotides, 1800 nucleotides, 2000 nucleotides, 2500 nucleotides, or 3000 nucleotides.

In some examples, the pseudo-random fragmentation methods provided herein are used to generate fragments wherein a particular percentage (or fraction) of the fragments generated fall within any of the size ranges described herein. For example, about 0%, 2%, 4%, 6%, 8%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% of the fragments generated may fall within any of the size ranges described herein.

Figure 4:
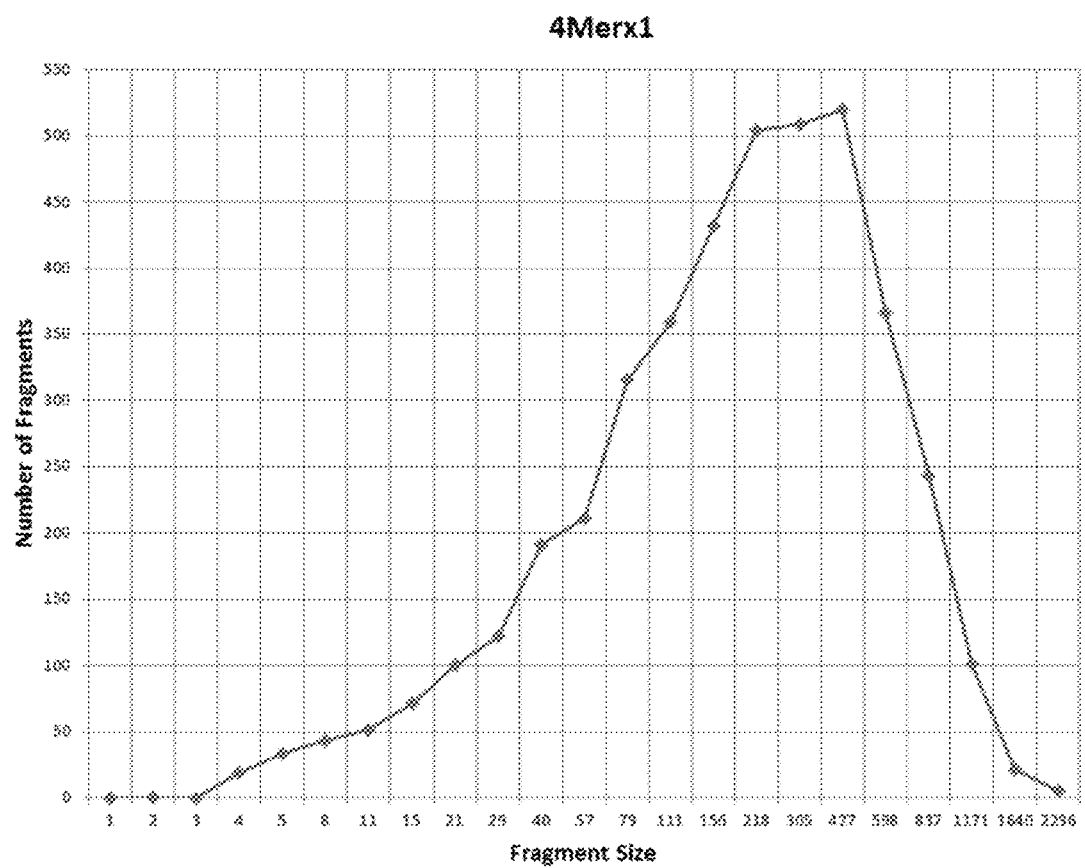
FIG. 4 shows a distribution of DNA fragment size after simulating generation of 1 Mbp random DNA sequences followed by cutting the sequences with a 4Mer cutter, CviQI (G/TAC).

In some examples multiple 4Mer cutters may be used to provide a distribution of about 18% of fragments of about 50 nucleotides or less, about 38% of fragments of about 200 nucleotides or less, about 25% of fragments between about 200 and about 400 nucleotides, and about 37% of fragments greater than about 400 nucleotides (e.g., see FIG. 4).

Additionally, the pseudo-random fragmentation method may be designed to minimize the percentage of fragments greater than a certain number of nucleotides in length, in order to minimize the loss of sequence information. For example, the method may be designed to yield less than about 0.1%, 0.5%, 1%, 2%, 5%, 10%, 20%, or 50% fragments greater than 100 nucleotides. The method may be designed to yield less than about 0.1%, 0.5%, 1%, 2%, 5%, 10%, 20%, or 50% fragments greater than 150 nucleotides.

The method may be designed to yield less than about 0.1%, 0.5%, 1%, 2%, 5%, 10%, 20%, or 50% fragments greater than 200 nucleotides. The method may be designed to yield less than about 0.1%, 0.5%, 1%, 2%, 5%, 10%, 20%, or 50% fragments greater than 300 nucleotides, and so on. As the ability of sequencing technologies to accurately read long DNA fragments increases, the pseudo-random fragmentation methods of the invention may be used to generate sequences suitable for any chosen read length.

Enzymes for use with the pseudo-random fragmentation method described herein may be chosen, for example, based on the length of their recognition site and their compatibility with certain buffer conditions (to allow for combination with other enzymes). Enzymes may also be chosen so that their cutting activity is methylation insensitive, or sensitive to methylation. For example, restriction enzymes with shorter recognition sites generally cut polynucleotides more frequently. Thus, cutting a target polynucleotide with a 6Mer cutter will generally produce more large fragments than cutting the same polynucleotide with a 4Mer cutter (e.g., compare FIGS. 3 and 4). Cutting a target polynucleotide with a plurality of enzymes (e.g. 2, 3, 4, 5, 6, 7, or more) may produce a greater number or fraction of fragments in the optimal size range for DNA sequencing than cutting with a single enzyme (see FIG. 5). Any restriction enzyme may be used with this method. Many are named in this specification, but others are known in the art.

This disclosure also provides methods of selecting a plurality of enzymes for pseudo-random fragmentation of a polynucleotide sequence. For example, a target polynucleotide may be exposed separately to 1, 2, 3, 4, 5, 6, 7, 8, 9, 10, 11, 12, 13, 14, 15, 16, 17, 18, 19, or 20 restriction enzymes. The size distribution of the target polynucleotide fragments is then determined, for example, by electrophoresis. The combination of enzymes providing the greatest number of fragments that are capable of being sequenced can then be chosen. The method can also be carried out in silico.

The enzymes may be disposed within the same partition, or within a plurality of partitions. For example, any of the plurality of enzyme number described herein may be disposed within a single partition, or across partitions. For example, a polynucleotide may be treated with about 2, 3, 4, 5, 6, 7, 8, 9, 10, 11, 12, 13, 14, 15, 16, 17, 18, 19, 20, 25, 30, 35, 45, 45, 50, or more restriction enzymes in the same partition, or across partitions. A polynucleotide may be treated with at least 2, 3, 4, 5, 6, 7, 8, 9, 10, 11, 12, 13, 14, 15, 16, 17, 18, 19, 20, 25, 30, 35, 45, 45, 50, or more restriction enzymes in the same partition, or across partitions. A polynucleotide may be treated with at least 2 but fewer than 4, 5, 6, 7, 8, 9, 10, 11, 12, 13, 14, 15, 16, 17, 18, 19, 20, 25, 30, 35, 45, 45, or 50 restriction enzymes in the same partition, or across partitions. A polynucleotide may be treated with about 2-4, 4-6, 6-8, 8-10, 10-12, 12-14, 14-16, 16-18, 18-20, 20-25, 25-30, 35-40, 40-45, or 45-50 restriction enzymes in the same partition, or across partitions.

The distribution of the restriction enzymes among the partitions will vary depending on the restriction enzymes, the target polynucleotide, and the desired fragment size. In some cases, each restriction enzyme may be distributed across an equivalent number of partitions, so that the number of partitions occupied by each restriction enzyme is equivalent. For example, if 10 restriction enzymes are used in a device containing 1,000 partitions, each enzyme may be present in 100 partitions. In other cases, each restriction enzyme may be distributed across a non-equivalent number of partitions, so that the number of partitions occupied by each restriction enzyme is not equivalent. For example, if 10 restriction enzymes are used in a device containing 1,000 partitions, enzymes 1-8 may be present in 100 partitions each, enzyme 9 may be present in 50 partitions, and enzyme 10 may be present in 150 partitions. Placement of restriction enzymes in an unequal number of partitions may be beneficial, for example, when an enzyme generates a desired product at a low yield. Placing this low-yield enzyme in more partitions will therefore expose more of the target polynucleotide to the enzyme, increasing the amount of the desired product (e.g., fragment of a certain size or composition) that can be formed from the enzyme. Such an approach may be useful for accessing portions of a target polynucleotide (e.g., a genome) that are not cut by enzymes producing polynucleotide fragments at a higher yield. The restriction site and efficiency of an enzyme, composition of the target polynucleotide, and efficiency and side-products generated by the enzyme may all be among the factors considered when determining how many partitions should receive a particular enzyme.

In some cases, different numbers of restriction enzymes may be used in a single partition and across all partitions. For example, 1, 2, 3, 4, 5, 6, 7, 8, 9, 10, 11, 12, 13, 14, 15, 16, 17, 18, 19, 20, 25, 30, 35, 45, 45, or 50 restriction enzymes or more may be used in each partition, while 2, 3, 4, 5, 6, 7, 8, 9, 10, 11, 12, 13, 14, 15, 16, 17, 18, 19, 20, 25, 30, 35, 45, 45, or 50 restriction enzymes or more may be used across all partitions. All combinations of these numbers are included within the invention. Non-limiting specific examples include the use of 1 restriction enzyme per partition and 2, 3, 4, 5, 6, 7, 8, 9, or 10 restriction enzymes across all partitions; 2 restriction enzymes per partition and 3, 4, 5, 6, 7, 8, 9, or 10 restriction enzymes across all partitions; 3 restriction enzymes per partition and 4, 5, 6, 7, 8, 9, or 10 restriction enzymes across all partitions; 4 restriction enzymes per partition and 5, 6, 7, 8, 9, or 10 restriction enzymes across all partitions; 5 restriction enzymes per partition and 6, 7, 8, 9, or 10 restriction enzymes across all partitions; 6 restriction enzymes per partition and 7, 8, 9, or 10 restriction enzymes across all partitions; 7 restriction enzymes per partition and 8, 9, or 10 restriction enzymes across all partitions; 8 restriction enzymes per partition and 9 or 10 restriction enzymes across all partitions; and 9 restriction enzymes per partition and 10 or more restriction enzymes across all partitions.

In some cases, at least 1, 2, 3, 4, 5, 6, 7, 8, 9, 10, 11, 12, 13, 14, 15, 16, 17, 18, 19, 20, 25, 30, 35, 45, 45, or 50 restriction enzymes or more may be used in each partition, while at least 2, 3, 4, 5, 6, 7, 8, 9, 10, 11, 12, 13, 14, 15, 16, 17, 18, 19, 20, 25, 30, 35, 45, 45, or 50 restriction enzymes or more may be used across all partitions. All combinations of these numbers are included within the invention. Non-limiting specific examples include the use of at least 1 restriction enzyme per partition and at least 2, 3, 4, 5, 6, 7, 8, 9, or 10 restriction enzymes across all partitions; at least 2 restriction enzymes per partition and at least 3, 4, 5, 6, 7, 8, 9, or 10 restriction enzymes across all partitions; at least 3 restriction enzymes per partition and at least 4, 5, 6, 7, 8, 9, or 10 restriction enzymes across all partitions; at least 4 restriction enzymes per partition and at least 5, 6, 7, 8, 9, or 10 restriction enzymes across all partitions; at least 5 restriction enzymes per partition and at least 6, 7, 8, 9, or 10 restriction enzymes across all partitions; at least 6 restriction enzymes per partition and at least 7, 8, 9, or 10 restriction enzymes across all partitions; at least 7 restriction enzymes per partition and at least 8, 9, or 10 restriction enzymes across all partitions; at least 8 restriction enzymes per partition and at least 9 or 10 restriction enzymes across all partitions; and at least 9 restriction enzymes per partition and at least 10 or more restriction enzymes across all partitions.

In some cases, at most 1, 2, 3, 4, 5, 6, 7, 8, 9, 10, 11, 12, 13, 14, 15, 16, 17, 18, 19, 20, 25, 30, 35, 45, 45, or 50 restriction enzymes or more may be used in each partition, while at most 2, 3, 4, 5, 6, 7, 8, 9, 10, 11, 12, 13, 14, 15, 16, 17, 18, 19, 20, 25, 30, 35, 45, 45, or 50 restriction enzymes or more may be used across all partitions. All combinations of these numbers are included within the invention. Non-limiting specific examples include the use of at most 1 restriction enzyme per partition and at most 2, 3, 4, 5, 6, 7, 8, 9, or 10 restriction enzymes across all partitions; at most 2 restriction enzymes per partition and at most 3, 4, 5, 6, 7, 8, 9, or 10 restriction enzymes across all partitions; at most 3 restriction enzymes per partition and at most 4, 5, 6, 7, 8, 9, or 10 restriction enzymes across all partitions; at most 4 restriction enzymes per partition and at most 5, 6, 7, 8, 9, or 10 restriction enzymes across all partitions; at most 5 restriction enzymes per partition and at most 6, 7, 8, 9, or 10 restriction enzymes across all partitions; at most 6 restriction enzymes per partition and at most 7, 8, 9, or 10 restriction enzymes across all partitions; at most 7 restriction enzymes per partition and at most 8, 9, or 10 restriction enzymes across all partitions; at most 8 restriction enzymes per partition and at most 9 or 10 restriction enzymes across all partitions; and at most 9 restriction enzymes per partition and at most 10 or more restriction enzymes across all partitions.

In some cases, at least 1, 2, 3, 4, 5, 6, 7, 8, 9, 10, 11, 12, 13, 14, 15, 16, 17, 18, 19, 20, 25, 30, 35, 45, 45, or 50 restriction enzymes or more may be used in each partition, while at most 2, 3, 4, 5, 6, 7, 8, 9, 10, 11, 12, 13, 14, 15, 16, 17, 18, 19, 20, 25, 30, 35, 45, 45, or 50 restriction enzymes or more may be used across all partitions. All combinations of these numbers are included within the invention. Non-limiting specific examples include the use of at least 1 restriction enzyme per partition and at most 2, 3, 4, 5, 6, 7, 8, 9, or 10 restriction enzymes across all partitions; at least 2 restriction enzymes per partition and at most 3, 4, 5, 6, 7, 8, 9, or 10 restriction enzymes across all partitions; at least 3 restriction enzymes per partition and at most 4, 5, 6, 7, 8, 9, or 10 restriction enzymes across all partitions; at least 4 restriction enzymes per partition and at most 5, 6, 7, 8, 9, or 10 restriction enzymes across all partitions; at least 5 restriction enzymes per partition and at most 6, 7, 8, 9, or 10 restriction enzymes across all partitions; at least 6 restriction enzymes per partition and at most 7, 8, 9, or 10 restriction enzymes across all partitions; at least 7 restriction enzymes per partition and at most 8, 9, or 10 restriction enzymes across all partitions; at least 8 restriction enzymes per partition and at most 9 or 10 restriction enzymes across all partitions; and at least 9 restriction enzymes per partition and at most 10 or more restriction enzymes across all partitions.

In some cases, at most 1, 2, 3, 4, 5, 6, 7, 8, 9, 10, 11, 12, 13, 14, 15, 16, 17, 18, 19, 20, 25, 30, 35, 45, 45, or 50 restriction enzymes or more may be used in each partition, while at least 2, 3, 4, 5, 6, 7, 8, 9, 10, 11, 12, 13, 14, 15, 16, 17, 18, 19, 20, 25, 30, 35, 45, 45, or 50 restriction enzymes or more may be used across all partitions. All combinations of these numbers are included within the invention. Non-limiting specific examples include the use of at most 1 restriction enzyme per partition and at least 2, 3, 4, 5, 6, 7, 8, 9, or 10 restriction enzymes across all partitions; at most 2 restriction enzymes per partition and at least 3, 4, 5, 6, 7, 8, 9, or 10 restriction enzymes across all partitions; at most 3 restriction enzymes per partition and at least 4, 5, 6, 7, 8, 9, or 10 restriction enzymes across all partitions; at most 4 restriction enzymes per partition and at least 5, 6, 7, 8, 9, or 10 restriction enzymes across all partitions; at most 5 restriction enzymes per partition and at least 6, 7, 8, 9, or 10 restriction enzymes across all partitions; at most 6 restriction enzymes per partition and at least 7, 8, 9, or 10 restriction enzymes across all partitions; at most 7 restriction enzymes per partition and at least 8, 9, or 10 restriction enzymes across all partitions; at most 8 restriction enzymes per partition and at least 9 or 10 restriction enzymes across all partitions; and at most 9 restriction enzymes per partition and at least 10 or more restriction enzymes across all partitions.

IV. Restriction Enzyme-Mediated Recycling

As described throughout this disclosure, certain methods of the invention involve the addition of barcodes, adapters, or other sequences to fragmented target polynucleotides. Barcodes may be polynucleotide barcodes, which may be ligated to the fragmented target polynucleotides or added via an amplification reaction. As described throughout this disclosure, fragmentation of target polynucleotides may be performed using one or more restriction enzymes contained within a partition (e.g., a microwell) where the fragmentation is performed. The partition may also contain a polynucleotide barcode and a ligase, which enables the attachment of the barcode to the fragmented polynucleotide. In some cases, an adapter may be used to make a fragmented target polynucleotide compatible for ligation with a barcode. The presence of adapters, fragmented target polynucleotide, barcodes, restriction enzymes, and ligases in the same partition may lead to the generation of undesirable side products that decrease the yield of a desired end product. For example, self-ligation may occur between adapters, target polynucleotide fragments, and/or barcodes. These self-ligations reduce the amount of starting material and decrease the yield of the desired product, for example, a polynucleotide fragment properly ligated to a barcode and/or and adapter.

This disclosure provides methods, compositions, systems, and devices for addressing this problem and increasing the yield of a desired product. The problem is addressed by pairing a first restriction enzyme and a second restriction enzyme. The two restriction enzymes create compatible termini upon cutting, but each enzyme has a different recognition sequence.

Ligation of two pieces of DNA generated after cutting with the first restriction enzyme will regenerate the recognition site for the first restriction enzyme, allowing the first restriction enzyme to re-cut the ligated DNA. Likewise, ligation of two pieces of DNA generated after cutting with the second restriction enzyme will regenerate the recognition site for the second restriction enzyme, allowing the second restriction enzyme to re-cut the ligated DNA. However, ligation of one piece of DNA generated after cutting with the first restriction enzyme and one piece of DNA generated after cutting with the second restriction enzyme will result in ligated DNA that is unrecognizable (and therefore uncuttable) by both the first and second enzymes. The result is that any multimers of fragmented target polynucleotides are re-cut and any multimers of adapter (or other molecules, e.g., barcodes) are also re-cut. However, when a fragmented target polynucleotide is properly ligated to an adapter (or barcode), the restriction sites for both enzymes are not present and the correctly ligated molecule may not be re-cut by either enzyme.

Figure 6:
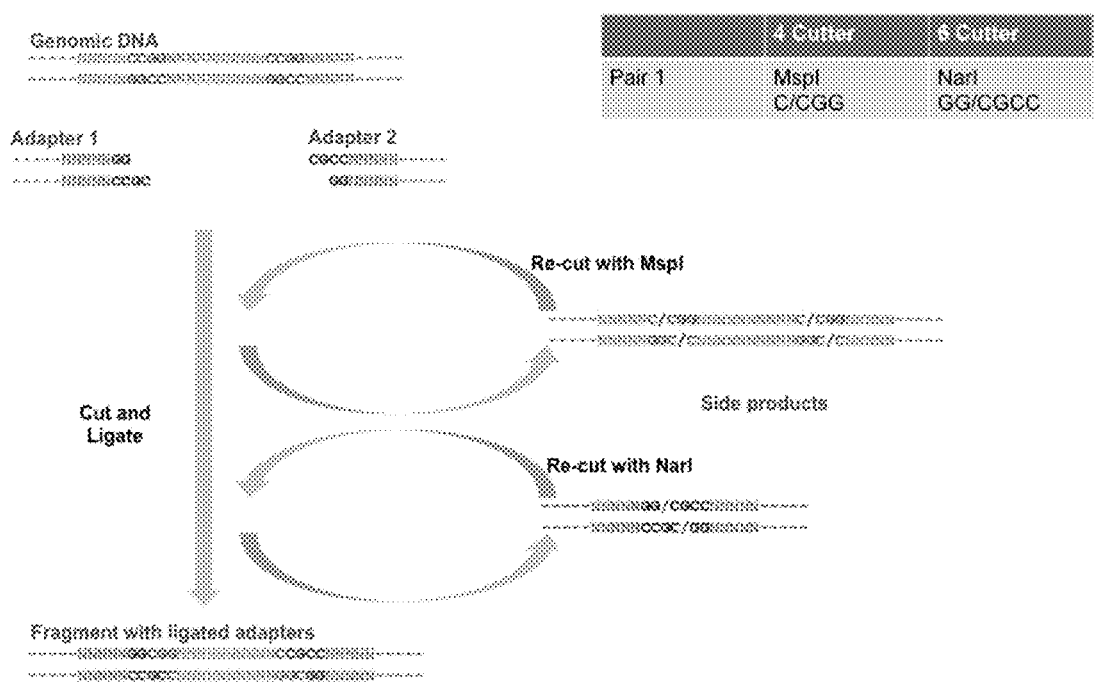
FIG. 6 shows the generation of unwanted byproducts ("Side products") during ligation of adapters to genomic DNA fragments and the recycling of the unwanted byproducts into starting materials ("Genomic DNA", "Adapter 1", and "Adapter 2") by paring of appropriate restriction enzymes (here, MspI and NarI).

An example of this method is illustrated in FIG. 6, and additional pairs of enzymes that may be used with the method are provided in FIGS. 7A-7B. Any pair of enzymes may be used, so long as they meet the following criteria: (1) the enzymes should create identical, or at least similar, ligatable termini upon cutting; and (2) the enzymes should have different recognition sequences. The enzymes may be selected to avoid or minimize cutting of certain polynucleotide sequences such as barcodes, adapters, and other polynucleotide components of a sample processing or preparation platform. The enzymes may be selected for methylation insensitivity or methylation sensitivity. The enzymes may also be selected to be active under s single set of environmental conditions, such as buffer conditions, temperature, etc. Minimizing the cutting of barcodes and adapters may be accomplished by pairing certain enzymes with certain barcodes and/or adapters.

This method may be used to increase the yield of any of the barcoding methods described herein. The regeneration of the starting materials (e.g., fragmented target polynucleotide, adapters, and barcodes) allows these starting materials another opportunity to form the desired products (i.e., fragmented target polynucleotides ligated to barcodes, optionally with adapters). This greatly increases the yield of the reaction and therefore decreases the amount of starting material required to produce the necessary amount of the desired products while limiting the amount of undesirable side products and lost sequence information.

The methods described above may be used to achieve about 75%, 85%, 95%, 96%, 97%, 98%, 99%, or 99.5% yield (w/w). The methods may be used to achieve at least about 75%, 85%, 95%, 96%, 97%, 98%, 99%, or 99.5% yield (w/w).

The methods described above may use, for example, a pair of restriction enzyme selected from the group consisting of MspI-NarI, BfaI-NarI, BfaI-NdeI, HinP1I-ClaI, MseI-NdeI, CviQI-NdeI, TaqαI-AcII, Rsal-PmeI, AluI-EcoRV, BstUI-PmeI, DpnI-StuI, HaeIII-PmeI, and HpyCH4V-SfoI. This list of enzymes is provided for purposes of illustration only, and is not meant to be limiting.

The methods described above may generally use any two enzymes that create ligatable termini upon cutting but that have different recognition sequences. However, the method is not limited to ligation. For example, multimers formed after amplification of side products formed by association of compatible ends could also be re-cut using the methods described above.

More than one pair of enzymes may also be used. The number of pairs of enzymes chosen will vary depending on the number of undesirable side products formed in a reaction. For example, 1, 2, 3, 4, 5, 6, 7, 8, 9, 10, 11, 12, 13, 14, 15, or more pairs of enzymes may be used. Treatment of a polynucleotide with the enzymes may be sequential, simultaneous, or both.

V. Preparation of Target Polynucleotides

Target polynucleotides processed according to the methods provided in this disclosure may be DNA, RNA, peptide nucleic acids, and any hybrid thereof, where the polynucleotide contains any combination of deoxyribo- and ribonucleotides. Polynucleotides may be single stranded or double stranded, as specified, or contain portions of both double stranded or single stranded sequence. Polynucleotides may contain any combination of nucleotides, including uracil, adenine, thymine, cytosine, guanine, inosine, xanthine, hypoxanthine, isocytosine, isoguanine and any nucleotide derivative thereof. As used herein, the term "nucleotide" may include nucleotides and nucleosides, as well as nucleoside and nucleotide analogs, and modified nucleotides, including both synthetic and naturally occurring species. Target polynucleotides may be cDNA, mitochondrial DNA (mtDNA), messenger RNA (mRNA), ribosomal RNA (rRNA), transfer RNA (tRNA), nuclear RNA (nRNA), small interfering RNA (siRNA), small nuclear RNA (snRNA), small nucleolar RNA (snoRNA), small Cajal body-specific RNA (scaRNA), microRNA (miRNA), double stranded (dsRNA), ribozyme, riboswitch or viral RNA. Target polynucleotides may be contained on a plasmid, cosmid, or chromosome, and may be part of a genome. In some cases, a target polynucleotide may comprise one or more genes and/or one or more pseudogenes. A pseudogene generally refers to a dysfunctional relative of a gene that has lost its protein coding ability and/or is otherwise no longer expressed in the cell.

Target polynucleotides may be obtained from a sample using any methods known in the art. A target polynucleotide processed as described herein may be obtained from whole cells, cell preparations and cell-free compositions from any organism, tissue, cell, or environment. In some instances, target polynucleotides may be obtained from bodily fluids which may include blood, urine, serum, lymph, saliva, mucosal secretions, perspiration, or semen. In some instances, polynucleotides may be obtained from environmental samples including air, agricultural products, water, and soil. In other instances polynucleotides may be the products of experimental manipulation including, recombinant cloning, polynucleotide amplification (as generally described in PCT/US99/01705), polymerase chain reaction (PCR) amplification, purification methods (such as purification of genomic DNA or RNA), and synthesis reactions.

Genomic DNA may be obtained from naturally occurring or genetically modified organisms or from artificially or synthetically created genomes. Target polynucleotides comprising genomic DNA may be obtained from any source and using any methods known in the art. For example, genomic DNA may be isolated with or without amplification. Amplification may include PCR amplification, multiple displacement amplification (MDA), rolling circle amplification and other amplification methods. Genomic DNA may also be obtained by cloning or recombinant methods, such as those involving plasmids and artificial chromosomes or other conventional methods (see Sambrook and Russell, *Molecular Cloning: A Laboratory Manual.*, cited supra.) Polynucleotides may be isolated using other methods known in the art, for example as disclosed in *Genome Analysis: A Laboratory Manual Series* (Vols. I-IV) or *Molecular Cloning: A Laboratory Manual*. If the isolated polynucleotide is an mRNA, it may be reverse transcribed into cDNA using conventional techniques, as described in Sambrook and Russell, *Molecular Cloning: A Laboratory Manual.*, cited supra.

Target polynucleotides may also be isolated from "target organisms" or "target cells". The terms "target organism" and "target cell" refer to an organism or cell, respectively, from which target polynucleotides may be obtained. Target cells may be obtained from a variety of organisms including human, mammal, non-human mammal, ape, monkey, chimpanzee, plant, reptilian, amphibian, avian, fungal, viral or bacterial organisms. Target cells may also be obtained from a variety of clinical sources such as biopsies, aspirates, blood, urine, formalin fixed embedded tissues, and the like. Target cells may comprise a specific cell type, such as a somatic cell, germline cell, wild-type cell, cancer or tumor cells, or diseased or infected cell. A target cell may refer to a cell derived from a particular tissue or a particular locus in a target organism. A target cell may comprise whole intact cells, or cell preparations.

Target polynucleotides may also be obtained or provided in specified quantities. Amplification may be used to increase the quantity of a target polynucleotide. Target polynucleotides may quantified by mass. For example, target polynucleotides may be provided in a mass ranging from about 1-10, 10-50, 50-100, 100-200, 200-1000, 1000-10000 ng. Target polynucleotides may be provided in a mass of at least about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, or 10000 ng. Target polynucleotides may be provided in a mass of less than about 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, or 10000 ng.

Target polynucleotides may also be quantified as "genome equivalents." A genome equivalent is an amount of polynucleotide equivalent to one haploid genome of an organism from which the target polynucleotide is derived. For example, a single diploid cell contains two genome equivalents of DNA. Target polynucleotides may be provided in an amount ranging from about 1-10, 10-50, 50-100, 100-1000, 1000-10000, 10000-100000, or 100000-1000000 genome equivalents. Target polynucleotides may be provided in an amount of at least about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000 70000, 80000, 90000, 100000, 200000, 300000, 400000, 500000, 600000, 700000, 800000, 900000, or 1000000 genome equivalents. Target polynucleotides may be provided in an amount less than about 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000 70000, 80000, 90000, 100000, 200000, 300000, 400000, 500000, 600000, 700000, 800000, 900000, or 1000000 genome equivalents.

Target polynucleotide may also be quantified by the amount of sequence coverage provided. The amount of sequence coverage refers to the average number of reads representing a given nucleotide in a reconstructed sequence. Generally, the greater the number of times a region is sequenced, the more accurate the sequence information obtained. Target polynucleotides may be provided in an amount that provides a range of sequence coverage from about 0.1×-10×, 10-×-50×, 50×-100×, 100×-200×, or 200×-500×. Target polynucleotide may be provided in an amount that provides at least about 0.1×, 0.2×, 0.3×, 0.4×, 0.5×, 0.6×, 0.7×, 0.8×, 0.9×, 1.0×, 5×, 10×, 25×, 50×, 100×, 125×, 150×, 175×, or 200× sequence coverage. Target polynucleotide may be provided in an amount that provides less than about 0.2×, 0.3×, 0.4×, 0.5×, 0.6×, 0.7×, 0.8×, 0.9×, 1.0×, 5×, 10×, 25×, 50×, 100×, 125×, 150×, 175×, or 200× sequence coverage.

VI. Fragmentation of Target Polynucleotides

Fragmentation of polynucleotides is used as a step in a variety of processing methods described herein. The size of the polynucleotide fragments, typically described in terms of length (quantified by the linear number of nucleotides per fragment), may vary depending on the source of the target polynucleotide, the method used for fragmentation, and the desired application. Moreover, while certain methods of the invention are illustrated using a certain number of fragmentation steps, the number of fragmentation steps provided is not meant to be limiting, and any number of fragmentation steps may be used. For example, 1, 2, 3, 4, 5, 6, 7, 8, 9, 10, 11, 12, 13, 14, 15, or more fragmentation steps may be used.

Fragments generated using the methods described herein may be about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides in length. Fragments generated using the methods described herein may be at least about 10, 20, 100, 200, 300, 400, 500, 1000, 5000, 10000, 100000, 250000, 500000, or more nucleotides in length. Fragments generated using the methods described herein may be less than about 10, 20, 100, 200, 300, 400, 500, 1000, 5000, 10000, 100000, 250000, 500000, nucleotides in length.

Fragments generated using the methods described herein may have a mean or median length of about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides. Fragments generated using the methods described herein may have a mean or median length of at least about 10, 20, 100, 200, 300, 400, 500, 1000, 5000, 10000, 100000, 250000, 500000, or more nucleotides. Fragments generated using the methods described herein may have a mean or median length of less than about 10, 20, 100, 200, 300, 400, 500, 1000, 5000, 10000, 100000, 250000, 500000, nucleotides.

Numerous fragmentation methods are described herein and known in the art. For example, fragmentation may be performed through physical, mechanical or enzymatic methods. Physical fragmentation may include exposing a target polynucleotide to heat or to UV light. Mechanical disruption may be used to mechanically shear a target polynucleotide into fragments of the desired range. Mechanical shearing may be accomplished through a number of methods known in the art, including repetitive pipetting of the target polynucleotide, sonication and nebulization. Target polynucleotides may also be fragmented using enzymatic methods. In some cases, enzymatic digestion may be performed using enzymes such as using restriction enzymes.

While the methods of fragmentation described in the preceding paragraph, and in some paragraphs of the disclosure, are described with reference to "target" polynucleotides, this is not meant to be limiting, above or anywhere else in this disclosure. Any means of fragmentation described herein, or known in the art, can be applied to any polynucleotide used with the invention. In some cases, this polynucleotide may be a target polynucleotide, such as a genome. In other cases, this polynucleotide may be a fragment of a target polynucleotide which one wishes to further fragment. In still other cases, still further fragments may be still further fragmented. Any suitable polynucleotide may be fragmented according the methods described herein.

A fragment of a polynucleotide generally comprises a portion of the sequence of the targeted polynucleotide from which the fragment was generated. In some cases, a fragment may comprise a copy of a gene and/or pseudogene, including one included in the original target polynucleotide. In some cases, a plurality of fragments generated from fragmenting a target polynucleotide may comprise fragments that each comprise a copy of a gene and/or pseudogene.

Restriction enzymes may be used to perform specific or non-specific fragmentation of target polynucleotides. The methods of the present disclosure may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide base pairs within a double stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single stranded DNA, called a "sticky end." In other cases, cleavage will not result in a fragment with an overhang, creating a "blunt end." The methods of the present disclosure may comprise use of restriction enzymes that generate either sticky ends or blunt ends.

Restriction enzymes may recognize a variety of recognition sites in the target polynucleotide. Some restriction enzymes ("exact cutters") recognize only a single recognition site (e.g., GAATTC). Other restriction enzymes are more promiscuous, and recognize more than one recognition site, or a variety of recognition sites. Some enzymes cut at a single position within the recognition site, while others may cut at multiple positions. Some enzymes cut at the same position within the recognition site, while others cut at variable positions.

The present disclosure provides method of selecting one or more restriction enzymes to produce fragments of a desired length. Polynucleotide fragmentation may be simulated in silico, and the fragmentation may be optimized to obtain the greatest number or fraction of polynucleotide fragments within a particular size range, while minimizing the number or fraction of fragments within undesirable size ranges. Optimization algorithms may be applied to select a combination of two or more enzymes to produce the desired fragment sizes with the desired distribution of fragments quantities.

A polynucleotide may be exposed to two or more restriction enzymes simultaneously or sequentially. This may be accomplished by, for example, adding more than one restriction enzyme to a partition, or by adding one restriction enzyme to a partition, performing the digestion, deactivating the restriction enzyme (e.g., by heat treatment) and then adding a second restriction enzyme. Any suitable restriction enzyme may be used alone, or in combination, in the methods presented herein.

Fragmenting of a target polynucleotide may occur prior to partitioning of the target polynucleotide or fragments generated from fragmenting. For example, genomic DNA (gDNA) may be fragmented, using, for example, a restriction enzyme, prior to the partitioning of its generated fragments. In another example, a target polynucleotide may be entered into a partition along with reagents necessary for fragmentation (e.g., including a restriction enzyme), such that fragmentation of the target polynucleotide occurs within the partition. For example, gDNA may be fragmented in a partition comprising a restriction enzyme, and the restriction enzyme is used to fragment the gDNA.

In some cases, a plurality of fragments may be generated prior to partitioning, using any method for fragmentation described herein. Some or all of the fragments of the plurality, for example, may each comprise a copy of a gene and/or a pseudogene. The fragments can be separated and partitioned such that each copy of the gene or pseudogene is located in a different partition. Each partition, for example, can comprise a different barcode sequence such that each copy of the gene and/or pseudogene can be associated with a different barcode sequence, using barcoding methods described elsewhere herein. Via the different barcode sequences, each gene and/or pseudogene can be counted and/or differentiated during sequencing of the barcoded fragments. Any sequencing method may be used, including those described herein.

For example, using restriction enzymes, genomic DNA (gDNA) can be fragmented to generate a plurality of non-overlapping fragments of the gDNA. At least some of the fragments of the plurality may each comprise a copy of a gene and/or a pseudogene. The fragments may be separated and partitioned such that each copy of the gene or pseudogene is located in a different partition. Each partition, for example, can comprise a different barcode sequence such that each copy of the gene and/or pseudogene may be barcoded with a different barcode sequence. Via the different barcode sequences, the genes and/or pseudogenes may be counted and or differentiated after sequencing of the barcoded fragments. Any sequencing method may be used, including those described herein.

IV. Partitioning of Polynucleotides

As described throughout the disclosure, certain methods, systems, and compositions of the disclosure may utilize partitioning of polynucleotides into separate partitions (e.g., microwells, droplets of an emulsion). These partitions may be used to contain polynucleotides for further processing, such as, for example, cutting, ligating, and/or barcoding.

Any number of devices, systems or containers may be used to hold, support or contain partitions of polynucleotides and their fragments. In some cases, partitions are formed from droplets, emulsions, or spots on a substrate. Weizmann et al. (*Nature Methods,* 2006, Vol. 3 No. 7 pages 545-550). Suitable methods for forming emulsions, which can be used as partitions or to generate microcapsules, include the methods described in Weitz et al. (U.S. Pub. No. 2012/0211084). Partitions may also be formed through the use of wells, microwells, multi-well plates, and microwell arrays. Partitioning may be performed using piezoelectric droplet generation (e.g., Bransky et al., *Lab on a Chip,* 2009, 9, 516-520). Partitioning may be performed using surface acoustic waves (e.g., Demirci and Montesano, *Lab on a Chip,* 2007, 7, 1139-1145).

Each partition may also contain, or be contained within any other suitable partition. For example, a well, microwell, hole, a surface of a bead, or a tube may comprise a droplet (e.g., a droplet in an emulsion), a continuous phase in an emulsion, a spot, a capsule, or any other suitable partition. A droplet may comprise a capsule, bead, or another droplet. A capsule may comprise a droplet, bead, or another capsule. These descriptions are merely illustrative, and all suitable combinations and pluralities are also envisioned. For example, any suitable partition may comprise a plurality of the same or different partitions. In one example, a well or microwell comprises a plurality of droplets and a plurality of capsules. In another example, a capsule comprises a plurality of capsules and a plurality of droplets. All combinations of partitions are envisioned. Table 1 shows non-limiting examples of partitions that may be combined with each other.

TABLE 1

Examples of partitions that may be combined with each other.

| | Well | Spot | Droplet | Capsule |
|---|---|---|---|---|
| Well | Well inside well | Spot inside well | Droplet inside well | Capsule inside well |

TABLE 1-continued

Examples of partitions that may be combined with each other.

|  | Well | Spot | Droplet | Capsule |
|---|---|---|---|---|
| Spot | Spot inside well | Spot inside spot | Droplet inside spot | Capsule inside spot |
| Droplet | Droplet inside well | Droplet inside spot | Droplet inside droplet | Droplet inside capsule<br>Capsule inside droplet |
| Capsule | Capsule inside well | Capsule inside spot<br>Spot inside capsule | Capsule inside droplet<br>Droplet inside capsule | Capsule inside capsule |
| Surface of a Bead | Bead inside well | Spot on bead<br>Bead inside spot | Bead inside droplet | Bead inside capsule |

Any partition described herein may comprise multiple partitions. For example, a partition may comprise 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. A partition may comprise at least 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, a partition may comprise less than 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, each partition may comprise 2-50, 2-20, 2-10, or 2-5 partitions.

The number of partitions employed may vary depending on the application. For example, the number of partitions may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 10000000, 20000000, or more. The number of partitions may be at least about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000, 000, 10000000, 20000000, or more. The number of partitions may be less than about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000, 000, 10000000, 20000000. The number of partitions may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

Such partitions may be pre-loaded with reagents to perform a particular reaction. For example, a capsule containing one or more reagents may be placed within a microwell. After adding a polynucleotide sample to the well, the capsule may be made to release its contents. The contents of the capsule may include, for example, restriction enzymes, ligases, barcodes, and adapters for processing the polynucleotide sample placed in the microwell.

In some cases, such partitions may be droplets of an emulsion. For example, a droplet of an emulsion may be an aqueous droplet in an oil phase. The droplet may comprise, for example, one or more reagents (e.g., restriction enzymes, ligases, polymerases, reagents necessary for nucleic acid amplification (e.g., primers, DNA polymerases, dNTPs, buffers)), a polynucleotide sample, and a barcode sequence. In some cases, the barcode sequence, polynucleotide sample, or any reagent may be associated with a solid surface within a droplet. In some cases, the solid surface is a bead. In some cases, the bead is a gel bead (see e.g., Agresti et al., U.S. Patent Publication No. 2010/0136544). In some cases the droplet is hardened into a gel bead (e.g., via polymerization).

A species may be contained within a droplet in an emulsion containing, for example, a first phase (e.g., oil or water) forming the droplet and a second (continuous) phase (e.g., water or oil). An emulsion may be a single emulsion, for example, a water-in-oil or an oil-in-water emulsion. An emulsion may be a double emulsion, for example a water-in-oil-in-water or an oil-in-water-in-oil emulsion. Higher-order emulsions are also possible. The emulsion may be held in any suitable container, including any suitable partition described in this disclosure.

In some cases, droplets in an emulsion comprise other partitions. A droplet in an emulsion may comprise any suitable partition including, for example, another droplet (e.g., a droplet in an emulsion), a capsule, a bead, and the like. Each partition may be present as a single partition or a plurality of partitions, and each partition may comprise the same species or different species.

In one example, a droplet in an emulsion comprises a capsule comprising reagents for sample processing. As described elsewhere in this disclosure, a capsule may contain one or more capsules, or other partitions. A sample comprising an analyte to be processed is contained within the droplet. A stimulus is applied to cause release of the contents of the capsule into the droplet, resulting in contact between the reagents and the analyte to be processed. The droplet is incubated under appropriate conditions for the processing of the analyte. Processed analyte may then be recovered. While this example describes an embodiment where a reagent is in a capsule and an analyte is in the droplet, the opposite configuration—i.e., reagent in the droplet and analyte in the capsule—is also possible.

The droplets in an emulsion may be of uniform size or heterogeneous size. In some cases, the diameter of a droplet in an emulsion may be about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. A droplet may have a diameter of at least about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a droplet may have a diameter of less than about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a droplet may have a diameter of about 0.001 µm to 1 mm, 0.01 µm to 900 µm, 0.1 µm to 600 µm, 100 µm to 200 µm, 100 µm to 300 µm, 100 µm to 400 µm, 100 µm to 500 µm, 100 µm to 600 µm, 150 µm to 200 µm, 150 µm to 300 µm, or 150 µm to 400 µm.

Droplets in an emulsion also may have a particular density. In some cases, the droplets are less dense than an aqueous fluid (e.g., water); in some cases, the droplets are denser than an aqueous fluid. In some cases, the droplets are less dense than a non-aqueous fluid (e.g., oil); in some cases, the droplets are denser than a non-aqueous fluid. Droplets may have a density of about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Droplets may have a density of at least about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. In other cases, droplet densities may be at most about 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Such densities can reflect the density of the capsule in any particular fluid (e.g., aqueous, water, oil, etc.)

Polynucleotides may be partitioned using a variety of methods. For example, polynucleotides may be diluted and dispensed across a plurality of partitions. A terminal dilution of a medium comprising polynucleotides may be performed such that the number of partitions or wells exceeds the number of polynucleotides. The ratio of the number of polynucleotides to the number of partitions may range from about 0.1-10, 0.5-10, 1-10, 2-10, 10-100, 100-1000, or more. The ratio of the number of polynucleotides to the number of partitions may be about 0.1, 0.5, 1, 2, 4, 8, 10, 20, 50, 100, or 1000. The ratio of the number of polynucleotides to the number of partitions may be at least about 0.1, 0.5, 1, 2, 4, 8, 10, 20, 50, 100, or 1000. The ratio of the number of polynucleotides to the number of partitions may be less than about 0.1, 0.5, 1, 2, 4, 8, 10, 20, 50, 100, or 1000.

The number of partitions employed may vary depending on the application. For example, the number of partitions may be about 5, 10, 50, 100, 250, 500, 750, 1000, 1500, 2000, 2500, 5000, 7500, or 10,000, or more. The number of partitions may be at least about 5, 10, 50, 100, 250, 500, 750, 1000, 1500, 2000, 2500, 5000, 7500, or 10,000, or more. The number of partitions may be less than about 5, 10, 50, 100, 250, 500, 750, 1000, 1500, 2000, 2500, 5000, 7500, or 10,000.

The volume of the partitions may vary depending on the application. For example, the volume of the partitions may be about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, or 5 nL. The volume of the partitions may be at least about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, or 5 nL. The volume of the partitions may be less than about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, or 5 nL.

Species may also be partitioned at a particular density. For example, species may be partitioned so that each partition contains about 1, 5, 10, 50, 100, 1000, 10000, 100000, or 1000000 species per partition. Species may be partitioned so that each partition contains at least about 1, 5, 10, 50, 100, 1000, 10000, 100000, 1000000 or more species per partition. Species may be partitioned so that each partition contains less than about 1, 5, 10, 50, 100, 1000, 10000, 100000, or 1000000 species per partition. Species may be partitioned such that each partition contains about 1-5, 5-10, 10-50, 50-100, 100-1000, 1000-10000, 10000-100000, or 100000-1000000 species per partition.

Species may be partitioned such that at least one partition comprises a species that is unique within that partition. This may be true for about 1%, 5%, 10%, 20%, 30%, 40%, 50%, 60%, 70%, 80%, 90%, or more of the partitions. This may be true for at least about 1%, 5%, 10%, 20%, 30%, 40%, 50%, 60%, 70%, 80%, 90%, or more of the partitions. This may be true for less than about 1%, 5%, 10%, 20%, 30%, 40%, 50%, 60%, 70%, 80%, or 90% of the partitions.

Particular polynucleotides may also be targeted to specific partitions. For example, in some cases, a capture reagent such as an oligonucleotide probe may be immobilized in a partition to capture specific polynucleotides through hybridization.

Polynucleotides may also be partitioned at a particular density. For example, polynucleotides may be partitioned such that each partition contains about 1-5, 5-10, 10-50, 50-100, 100-1000, 1000-10000, 10000-100000, or 100000-1000000 polynucleotides per partition. Polynucleotides may be partitioned so that each partition contains about 1, 5, 10, 50, 100, 1000, 10000, 100000, 1000000 or more polynucleotides per partition. Polynucleotides may be partitioned so that each partition contains less than about 1, 5, 10, 50, 100, 1000, 10000, 100000, or 1000000 polynucleotides per partition. Polynucleotides may be partitioned so that each partition contains at least about 1, 5, 10, 50, 100, 1000, 10000, 100000, or 1000000 polynucleotides per partition.

Polynucleotides may be partitioned such that at least one partition comprises a polynucleotide sequence with a unique sequence compared to all other polynucleotide sequences contained within the same partition. This may be true for about 1%, 5%, 10%, 20%, 30%, 40%, 50%, 60%, 70%, 80%, 90%, or more of the partitions. This may be true for less than about 1%, 5%, 10%, 20%, 30%, 40%, 50%, 60%, 70%, 80%, 90%, or more of the partitions. This may be true for more than about 1%, 5%, 10%, 20%, 30%, 40%, 50%, 60%, 70%, 80%, 90%, or more of the partitions.

V. Barcoding

Downstream applications, for example DNA sequencing, may rely on the barcodes to identify the origin of a sequence and, for example, to assemble a larger sequence from sequenced fragments. Therefore, it may be desirable to add barcodes to the polynucleotide fragments generated by the methods described herein. Barcodes may be of a variety of different formats, including polynucleotide barcodes. Depending upon the specific application, barcodes may be attached to polynucleotide fragments in a reversible or irreversible manner. Barcodes may also allow for identification and/or quantification of individual polynucleotide fragments during sequencing.

Barcodes may be loaded into partitions so that one or more barcodes are introduced into a particular partition. Each partition may contain a different set of barcodes. This may be accomplished by directly dispensing the barcodes into the partitions, enveloping the barcodes (e.g., in a droplet of an emulsion), or by placing the barcodes within a container that is placed in a partition (e.g., a microcapsule).

The number of partitions employed may vary depending on the application. For example, the number of partitions may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 10000000, 20000000, or more. The number of partitions may be at least about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 10000000, 20000000, or more. The number of partitions may be less than about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 10000000, 20000000. The number of partitions may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

The number of different barcodes or different sets of barcodes that are partitioned may vary depending upon, for example, the particular barcodes to be partitioned and/or the application. Different sets of barcodes may be, for example, sets of identical barcodes where the identical barcodes differ between each set. Or different sets of barcodes may be, for example, sets of different barcodes, where each set differs in its included barcodes. For example, about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, less than about 1, 5, 10, 50, 100, 1000, 10000, 20000, 30000, 40000, 50000, 60000, 70000, 80000, 90000, 100000, 200,000, 300,000, 400,000, 500,000, 600, 000, 700,000, 800,000, 900,000, 1000000, 2000000, 3000000, 4000000, 5000000, 6000000, 7000000, 8000000, 9000000, 10000000, 20000000, 50000000, or 100000000 different barcodes or different sets of barcodes may be partitioned. In some examples, about 1-5, 5-10, 10-50, 50-100, 100-1000, 1000-10000, 10000-100000, 100000-1000000, 10000-1000000, 10000-10000000, or 10000-100000000 barcodes may be partitioned.

Barcodes may be partitioned at a particular density. For example, barcodes may be partitioned so that each partition contains about 1, 5, 10, 50, 100, 1000, 10000, 20,000, 30,000, 40,000, 50,000, 60,000, 70,000, 80,000, 90,000, 100,000, 200,000, 300,000, 400,000, 500,000, 600,000, 700, 000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600, 000, 700,000, 800,000, 900,000, 1000000, 2000000, 3000000, 4000000, 5000000, 6000000, 7000000, 8000000, 9000000, 10000000, 20000000, 50000000, 100000000, or more barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 barcodes per partition.

Barcodes may be partitioned such that identical barcodes are partitioned at a particular density. For example, identical barcodes may be partitioned so that each partition contains about 1, 5, 10, 50, 100, 1000, 10000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, 20000000, 50000000, or 100000000 identical barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800, 000, 900,000, 1000000, 2000000, 3000000, 4000000, 5000000, 6000000, 7000000, 8000000, 9000000, 10000000, 20000000, 50000000, 100000000, or more identical barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600, 000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 identical barcodes per partition.

Barcodes may be partitioned such that different barcodes are partitioned at a particular density. For example, different barcodes may be partitioned so that each partition contains about 1, 5, 10, 50, 100, 1000, 10000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, 20000000, 50000000, or 100000000 different barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800, 000, 900,000, 1000000, 2000000, 3000000, 4000000, 5000000, 6000000, 7000000, 8000000, 9000000, 10000000, 20000000, 50000000, 100000000, or more different barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 different barcodes per partition.

The number of partitions employed to partition barcodes may vary, for example, depending on the application and/or the number of different barcodes to be partitioned. For example, the number of partitions employed to partition barcodes may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 10000000, 20000000 or more. The number of partitions employed to partition barcodes may be at least about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000 or more. The number of partitions employed to partition barcodes may be less than about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or 20000000. The number of partitions employed to partition barcodes may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000. As described above, different barcodes or different sets of barcodes (e.g., each set comprising a plurality of identical barcodes or different barcodes) may be partitioned such that each partition comprises a different barcode or different barcode set. In some cases, each partition may comprise a different set of identical barcodes. Where different sets of identical barcodes are partitioned, the number of identical barcodes per partition may vary. For example, about 100,000 or more different sets of identical barcodes may be partitioned across about 100,000 or more different partitions, such that each partition comprises a different set of identical barcodes. In each partition, the number of identical barcodes per set of barcodes may be about 1,000,000 identical barcodes. In some cases, the number of different sets of barcodes may be equal to or substantially equal to the number of partitions. Any suitable number of different barcodes or different barcode sets (including numbers of different barcodes or different barcode sets to be partitioned described elsewhere herein), number of barcodes per partition (including numbers of barcodes per partition described elsewhere herein), and number of partitions (including numbers of partitions described elsewhere herein) may be combined to generate a diverse library of partitioned barcodes with high numbers of barcodes per partition. Thus, as will be appreciated, any of the above-described different numbers of barcodes may be provided with any of the above-described barcode densities per partition, and in any of the above-described numbers of partitions.

For example, a population of microcapsules may be prepared such that a first microcapsule in the population comprises multiple copies of identical barcodes (e.g., polynucleotide bar codes, etc.) and a second microcapsule in the population comprises multiple copies of a barcode that differs from the barcode within the first microcapsule. In some cases, the population of microcapsules may comprise multiple microcapsules (e.g., greater than about 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules), each containing multiple copies of a barcode that differs from that contained in the other microcapsules. In some cases, the population may comprise greater than about 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules with identical sets of barcodes. In some cases, the population may comprise greater than about 2, 3, 4, 5, 6, 7, 8, 9, 10, 15, 20, 25, 30, 35, 40, 45, 50, 100, 500, 1000, 5000, 10000, 100000, 1000000, 10000000, 100000000, or 1000000000 microcapsules, wherein the microcapsules each comprise a different combination of barcodes. For example, in some cases the different combinations overlap, such that a first microcapsule may comprise, e.g., barcodes A, B, and C, while a second microcapsule may comprise barcodes A, B, and D. In another example, the different combinations do not overlap, such that a first microcapsule may comprise, e.g., barcodes A, B, and C, while a second microcapsule may comprise barcodes D, E, and F. The use of microcapsules is, of course, optional. All of the combinations described above, and throughout this disclosure, may also be generated by dispending barcodes (and other reagents) directly into partitions (e.g., microwells).

The barcodes may be loaded into the partitions at an expected or predicted ratio of barcodes per species to be barcoded (e.g., polynucleotide fragment, strand of polynucleotide, cell, etc.). In some cases, the barcodes are loaded into partitions such that more than about 1, 2, 3, 4, 5, 6, 7, 8, 9, 10, 20, 50, 100, 500, 1000, 5000, 10000, or 200000 barcodes are loaded per species. In some cases, the barcodes are loaded in the partitions so that less than about 1, 2, 3, 4, 5, 6, 7, 8, 9, 10, 20, 50, 100, 500, 1000, 5000, 10000, or 200000 barcodes are loaded per species. In some cases, the average number of barcodes loaded per species is less than, or greater than, about 0.0001, 0.001, 0.01, 0.1, 1, 2, 3, 4, 5, 6, 7, 8, 9, 10, 20, 50, 100, 500, 1000, 5000, 10000, or 200000 barcodes per species.

When more than one barcode is present per polynucleotide fragment, such barcodes may be copies of the same barcode, or multiple different barcodes. For example, the attachment process may be designed to attach multiple identical barcodes to a single polynucleotide fragment, or multiple different barcodes to the polynucleotide fragment.

The methods provided herein may comprise loading a partition (e.g., a microwell, droplet of an emulsion) with the reagents necessary for the attachment of barcodes to polynucleotide fragments. In the case of ligation reactions, reagents including restriction enzymes, ligase enzymes, buffers, adapters, barcodes and the like may be loaded into a partition. In the case barcoding by amplification, reagents including primers, DNA polymerases, DNTPs, buffers, barcodes and the like may be loaded into a partition. As described throughout this disclosure, these reagents may be loaded directly into the partition, or via a container such as a microcapsule. If the reagents are not disposed within a container, they may be loaded into a partition (e.g., a microwell) which may then be sealed with a wax or oil until the reagents are used.

Barcodes may be ligated to a polynucleotide fragment using sticky or blunt ends. Barcoded polynucleotide fragments may also be generated by amplifying a polynucleotide fragment with primers comprising barcodes.

Barcodes may be assembled combinatorially, from smaller components designed to assemble in a modular format. For example, three modules, 1A, 1B, and 1C may be combinatorially assembled to produce barcode 1ABC. Such combinatorial assembly may significantly reduce the cost of synthesizing a plurality of barcodes. For example, a combinatorial system consisting of 3 A modules, 3 B modules, and 3 C modules may generate 3*3*3=27 possible barcode sequences from only 9 modules.

VI. Microcapsules and Microwell Capsule Arrays

Microcapsules and microwell capsule array (MCA) devices may be used to perform the polynucleotide processing methods described herein. MCA devices are devices with a plurality of microwells. Microcapsules are introduced into these microwells, before, after, or concurrently with the introduction of a sample.

Microwells may comprise free reagents and/or reagents encapsulated in microcapsules. Any of the reagents described in this disclosure may be encapsulated in a microcapsule, including any chemicals, particles, and elements suitable for sample processing reactions involving a polynucleotide. For example, a microcapsule used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, dNTPs, ddNTPs and the like.

Additional exemplary reagents include: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, oligonucleotides, nucleotides, deoxyribonucleotide triphosphates (dNTPs), dideoxyribonucleotide triphosphates (ddNTPs), DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, micro-RNA, dsRNA, ribozyme, riboswitch and viral RNA, polymerase, ligase, restriction enzymes, proteases, nucleases, protease inhibitors, nuclease inhibitors, chelating agents, reducing agents, oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds.

In some cases, a microcapsule comprises a set of reagents that have a similar attribute (e.g., a set of enzymes, a set of minerals, a set of oligonucleotides, a mixture of different bar-codes, a mixture of identical bar-codes). In other cases, a microcapsule comprises a heterogeneous mixture of reagents. In some cases, the heterogeneous mixture of reagents comprises all components necessary to perform a reaction. In some cases, such mixture comprises all components necessary to perform a reaction, except for 1, 2, 3, 4, 5, or more components necessary to perform a reaction. In some cases, such additional components are contained within a different microcapsule or within a solution within a partition (e.g., microwell) of the device.

In some cases, only microcapsules comprising reagents are introduced. In other cases, both free reagents and reagents encapsulated in microcapsules are loaded into the device, either sequentially or concurrently. In some cases, reagents are introduced to the device either before or after a particular step. In some cases, reagents and/or microcapsules comprising reagents are introduced sequentially such that different reactions or operations occur at different steps. The reagents (or microcapsules) may be also be loaded at steps interspersed with a reaction or operation step. For example, microcapsules comprising reagents for fragmenting polynucleotides (e.g., restriction enzymes) may be loaded into the device, followed by loading of microcapsules comprising reagents for ligating bar-codes and subsequent ligation of the bar-codes to the fragmented molecules.

Microcapsules may be pre-formed and filled with reagents by injection. For example, the picoinjection methods described in Abate et al. (Proc. Natl. Acad. Sci. U.S.A., 2010, 107(45), 19163-19166) and Weitz et al. (U.S. Pub. No. 2012/0132288) may be used to introduce reagents into the interior of microcapsules described herein. These methods can also be used to introduce a plurality of any of the reagents described herein into microcapsules.

Microcapsules may be formed by any emulsion technique known in the art. For example, the multiple emulsion technique of Weitz et al. (U.S. Pub. No. 2012/0211084) may be used to form microcapsules (or partitions) for use with the methods disclosed herein.

Numerous chemical triggers may be used to trigger the disruption of partitions (e.g., Plunkett et al., Biomacromolecules, 2005, 6:632-637). Examples of these chemical changes may include, but are not limited to pH-mediated changes to the integrity of a component of a partition, disintegration of a component of a partition via chemical cleavage of crosslink bonds, and triggered depolymerization of a component of a partition. Bulk changes may also be used to trigger disruption of partitions.

A change in pH of a solution, such as a decrease in pH, may trigger disruption of a partition via a number of different mechanisms. The addition of acid may cause degradation or disassembly a portion of a partition through a variety of mechanisms. Addition of protons may disassemble cross-linking of polymers in a component of a partition, disrupt ionic or hydrogen bonds in a component of a partition, or create nanopores in a component of a partition to allow the inner contents to leak through to the exterior. A change in pH may also destabilize an emulsion, leading to release of the contents of the droplets.

In some examples, a partition is produced from materials that comprise acid-degradable chemical cross-linkers, such a ketals. A decrease in pH, particular to a pH lower than 5, may induce the ketal to convert to a ketone and two alcohols and facilitate disruption of the partition. In other examples, the partitions may be produced from materials comprising one or more polyelectrolytes that are pH sensitive. A decrease in pH may disrupt the ionic- or hydrogen-bonding interactions of such partitions, or create nanopores therein. In some cases, partitions made from materials comprising polyelectrolytes comprise a charged, gel-based core that expands and contracts upon a change of pH.

Disruption of cross-linked materials comprising a partition can be accomplished through a number of mechanisms. In some examples, a partition can be contacted with various chemicals that induce oxidation, reduction or other chemical changes. In some cases, a reducing agent, such as beta-mercaptoethanol, can be used, such that disulfide bonds of a partition are disrupted. In addition, enzymes may be added to cleave peptide bonds in materials forming a partition, thereby resulting in a loss of integrity of the partition.

Depolymerization can also be used to disrupt partitions. A chemical trigger may be added to facilitate the removal of a protecting head group. For example, the trigger may cause removal of a head group of a carbonate ester or carbamate within a polymer, which in turn causes depolymerization and release of species from the inside of a partition.

In yet another example, a chemical trigger may comprise an osmotic trigger, whereby a change in ion or solute concentration in a solution induces swelling of a material used to make a partition. Swelling may cause a buildup of internal pressure such that a partition ruptures to release its contents. Swelling may also cause an increase in the pore size of the material, allowing species contained within the partition to diffuse out, and vice versa.

A partition may also be made to release its contents via bulk or physical changes, such as pressure induced rupture, melting, or changes in porosity.

VII. Polynucleotide Sequencing

Generally, the methods and compositions provided herein are useful for preparation of polynucleotide fragments for downstream applications such as sequencing. Sequencing may be performed by any available technique. For example, sequencing may be performed by the classic Sanger sequencing method. Sequencing methods may also include: high-throughput sequencing, pyrosequencing, sequencing-by-synthesis, single-molecule sequencing, nanopore sequencing, sequencing-by-ligation, sequencing-by-hybridization, RNA-Seq (Illumina), Digital Gene Expression (Helicos), next generation sequencing, single molecule sequencing by synthesis (SMSS) (Helicos), massively-parallel sequencing, clonal single molecule Array (Solexa), shotgun sequencing, Maxim-Gilbert sequencing, primer walking, and any other sequencing methods known in the art.

In some cases varying numbers of fragments are sequenced. For example, in some cases about 30%-90% of the fragments are sequenced. In some cases, about 35%-85%, 40%-80%, 45%-75%, 50%-70%, 55%-65%, or 50%-60% of the fragments are sequenced. In some cases, at least about 30%, 40%, 50%, 60%, 70%, 80%, or 90% of the fragments are sequenced. In some cases less than about 30%, 40%, 50%, 60%, 70%, 80%, or 90% of the fragments are sequenced.

In some cases sequences from fragments are assembled to provide sequence information for a contiguous region of the original target polynucleotide that is longer than the individual sequence reads. Individual sequence reads may be about 10-50, 50-100, 100-200, 200-300, 300-400, or more nucleotides in length.

The identities of the barcode tags may serve to order the sequence reads from individual fragments as well as to differentiate between haplotypes. For example, during the partitioning of individual fragments, parental polynucleotide fragments may separated into different partitions. With an increase in the number of partitions, the likelihood of a fragment from both a maternal and paternal haplotype contained in the same partition becomes negligibly small. Thus, sequence reads from fragments in the same partition may be assembled and ordered.

VIII. Polynucleotide Phasing

This disclosure also provides methods and compositions to prepare polynucleotide fragments in such a manner that may enable phasing or linkage information to be generated. Such information may allow for the detection of linked genetic variations in sequences, including genetic variations (e.g., SNPs, mutations, indels, copy number variations, transversions, translocations, inversions, etc.) that are separated by long stretches of polynucleotides. The term "indel" refers to a mutation resulting in a colocalized insertion and deletion and a net gain or loss in nucleotides. A "microindel" is an indel that results in a net gain or loss of 1 to 50 nucleotides. These variations may exist in either a cis or trans relationship. In a cis relationship, two or more genetic variations exist in the same polynucleotide or strand. In a trans relationship, two or more genetic variations exist on multiple polynucleotide molecules or strands.

Methods provided herein may be used to determine polynucleotide phasing. For example, a polynucleotide sample (e.g., a polynucleotide that spans a given locus or loci) may be partitioned such that at most one molecule of polynucleotide is present per partition (e.g., microwell). The polynucleotide may then be fragmented, barcoded, and sequenced. The sequences may be examined for genetic variation. The detection of genetic variations in the same sequence tagged with two different bar codes may indicate that the two genetic variations are derived from two separate strands of DNA, reflecting a trans relationship. Conversely, the detection of two different genetic variations tagged with the same bar codes may indicate that the two genetic variations are from the same strand of DNA, reflecting a cis relationship.

Phase information may be important for the characterization of a polynucleotide fragment, particularly if the polynucleotide fragment is derived from a subject at risk of, having, or suspected of a having a particular disease or disorder (e.g., hereditary recessive disease such as cystic fibrosis, cancer, etc.). The information may be able to distinguish between the following possibilities: (1) two genetic variations within the same gene on the same strand of DNA and (2) two genetic variations within the same gene but located on separate strands of DNA. Possibility (1) may indicate that one copy of the gene is normal and the individual is free of the disease, while possibility (2) may indicate that the individual has or will develop the disease, particularly if the two genetic variations are damaging to the function of the gene when present within the same gene copy. Similarly, the phasing information may also be able to distinguish between the following possibilities: (1) two genetic variations, each within a different gene on the same strand of DNA and (2) two genetic variations, each within a different gene but located on separate strands of DNA.

IX. Sequencing Polynucleotides from Small Numbers of Cells

Methods provided herein may also be used to prepare polynucleotide contained within cells in a manner that enables cell-specific information to be obtained. The methods enable detection of genetic variations (e.g., SNPs, mutations, indels, copy number variations, transversions, translocations, inversions, etc.) from very small samples, such as from samples comprising about 10-100 cells. In some cases, about 1, 5, 10, 20, 30, 40, 50, 60, 70, 80, 90 or 100 cells may be used in the methods described herein. In some cases, at least about 1, 5, 10, 20, 30, 40, 50, 60, 70, 80, 90 or 100 cells may be used in the methods described herein. In other cases, at most about 5, 10, 20, 30, 40, 50, 60, 70, 80, 90 or 100 cells may be used in the methods described herein.

In an example, a method comprises partitioning a cellular sample (or crude cell extract) such that at most one cell (or extract of one cell) is present per partition, lysing the cells, fragmenting the polynucleotides contained within the cells by any of the methods described herein, attaching the fragmented polynucleotides to barcodes, pooling, and sequencing.

As described elsewhere herein, the barcodes and other reagents may be contained within a microcapsule. These microcapsules may be loaded into a partition (e.g., a microwell) before, after, or concurrently with the loading of the cell, such that each cell is contacted with a different microcapsule. This technique may be used to attach a unique barcode to polynucleotides obtained from each cell. The resulting tagged polynucleotides may then be pooled and sequenced, and the barcodes may be used to trace the origin of the polynucleotides. For example, polynucleotides with identical barcodes may be determined to originate from the same cell, while polynucleotides with different barcodes may be determined to originate from different cells.

The methods described herein may be used to detect the distribution of oncogenic mutations across a population of cancerous tumor cells. For example, some tumor cells may have a mutation, or amplification, of an oncogene (e.g., HER2, BRAF, EGFR, KRAS) in both alleles (homozygous), others may have a mutation in one allele (heterozygous), and still others may have no mutation (wild-type). The methods described herein may be used to detect these differences, and also to quantify the relative numbers of homozygous, heterozygous, and wild-type cells. Such information may be used, for example, to stage a particular cancer and/or to monitor the progression of the cancer and its treatment over time.

In some examples, this disclosure provides methods of identifying mutations in two different oncogenes (e.g., KRAS and EGFR). If the same cell comprises genes with both mutations, this may indicate a more aggressive form of cancer. In contrast, if the mutations are located in two different cells, this may indicate that the cancer is more benign, or less advanced.

X. Analysis of Gene Expression

Methods of the disclosure may be applicable to processing samples for the detection of changes in gene expression. A sample may comprise a cell, mRNA, or cDNA reverse transcribed from mRNA. The sample may be a pooled sample, comprising extracts from several different cells or tissues, or a sample comprising extracts from a single cell or tissue.

Cells may be placed directly into an partition (e.g., a microwell) and lysed. After lysis, the methods of the invention may be used to fragment and barcode the polynucleotides of the cell for sequencing. Polynucleotides may also be extracted from cells prior to introducing them into a partition used in a method of the invention. Reverse transcription of mRNA may be performed in a partition described herein, or outside of such a partition. Sequencing cDNA may provide an indication of the abundance of a particular transcript in a particular cell over time, or after exposure to a particular condition.

The methods presented throughout this disclosure provide several advantages over current polynucleotide processing methods. First, inter-operator variability is greatly reduced. Second, the methods may be carried out in microfluidic devices, which have a low cost and can be easily fabricated. Third, the controlled fragmentation of the target polynucleotides allows the user to produce polynucleotide fragments with a defined and appropriate length. This aids in partitioning the polynucleotides and also reduces the amount of sequence information loss due to the present of overly-large fragments. The methods and systems also provide a facile workflow that maintains the integrity of the processed polynucleotide. Additionally, the use of restriction enzymes enables the user to create DNA overhangs ("sticky ends") that may be designed for compatibility with adapters and/or barcodes.

EXAMPLES

Example 1

Generation of Non-Overlapping DNA Fragments for Sequencing

This example demonstrates a method for the generation of non-overlapping DNA fragments suitable for DNA sequencing and other downstream applications. An implementation of this method is schematically illustrated in FIG. 2.

Figure 2:
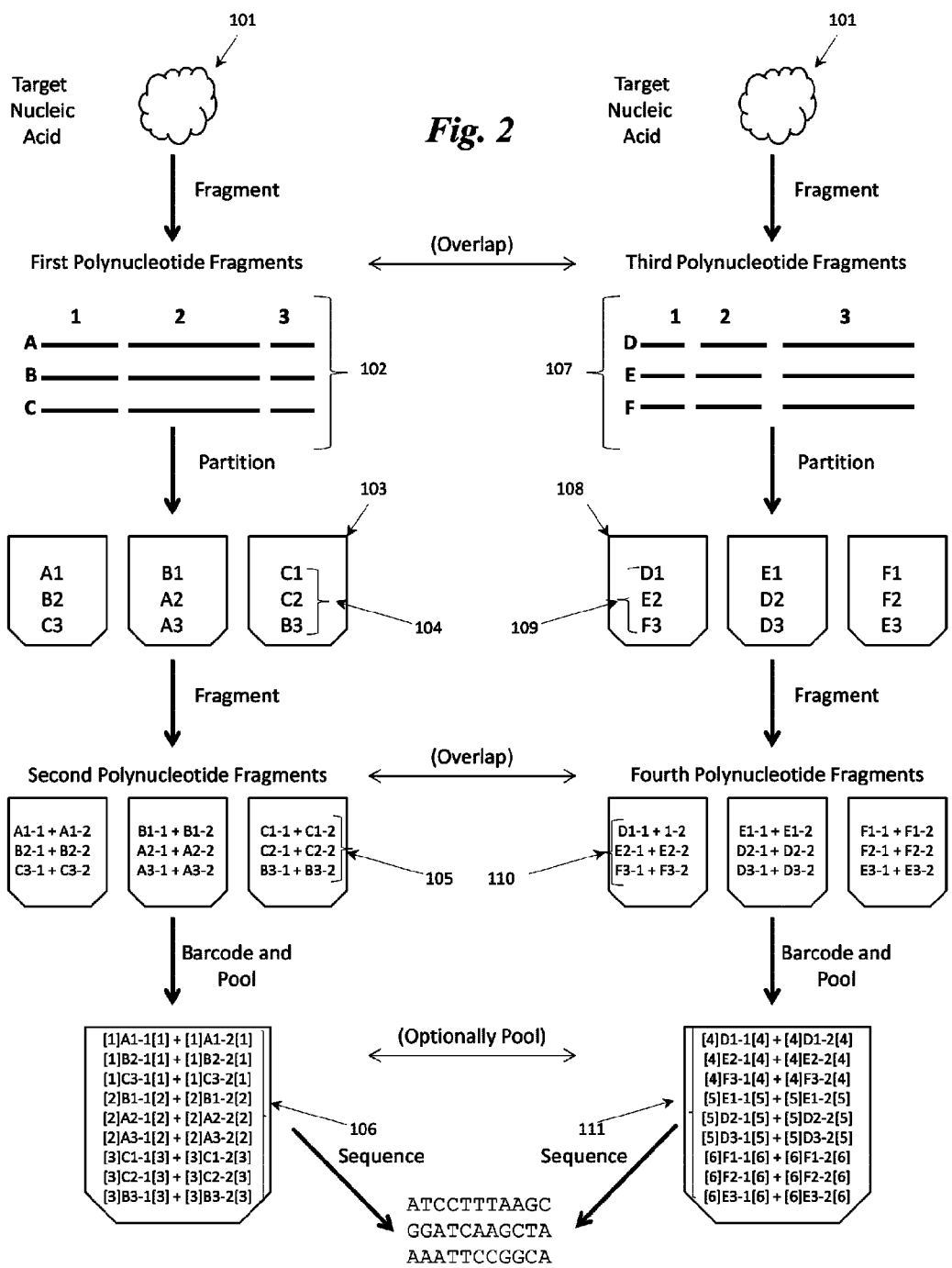
FIG. 2 is a schematic representation of methods of generating non-overlapping DNA fragments for DNA sequencing.

With reference to FIG. 2, a target polynucleotide 101, genomic DNA, is fragmented with the enzyme NotI, to generate a plurality of non-overlapping first polynucleotide fragments 102. The first polynucleotide fragments are partitioned into separate microwells 103 in a microdevice such that each microwell comprises a plurality of fragments, but only a single fragment with a particular sequence 104. The left-hand side of FIG. 2 illustrates three microwells (one is labeled 103), each containing three exemplary unique fragments 104, corresponding to the first polynucleotide fragments 102. Referring again to the left-hand side of FIG. 2, the left-most well contains fragments A1, B2, and C3, the middle well contains fragments B1, A2, and A3, and the right-most well contains fragments C1, C2, and B3.

The partitioned fragments are then further fragmented, to generate a plurality of non-overlapping second polynucleotide fragments 105. Referring again to the left-hand side of FIG. 2, each member of the second polynucleotide fragments is designated by its first fragment identifier (e.g., A1, B2, etc.), followed by a "-1" or a "-2". For example, first fragment A1 is fragmented to produce second fragments A1-1 and A1-2. First fragment B2 is fragmented to produce second fragments B2-1 and B2-2, and so on. For the sake of simplicity, only two second fragments are shown for each first fragment. This is, of course, not meant to be limiting, as any number of fragments may be generated at any step of the process.

The second set polynucleotide fragments are barcoded, and the barcoded sequences are pooled. Referring to the lower left-hand side of FIG. 2, the labels [1], [2], and [3] represent three different barcode sequences used to label the second fragments 105. The labeled sequences are designated 106. Optionally, adapter sequences (not shown) are used to make the second fragments 105 compatible for ligation with the barcodes. The barcoding is performed while the fragments are still partitioned, before pooling. The pooled barcoded sequences are then sequenced.

With continued reference to FIG. 2, the methods described above are then repeated, using a second rare cutter enzyme, XmaIII to digest the genomic DNA and generate a plurality of non-overlapping third polynucleotide fragments 107. The third polynucleotide fragments and the first polynucleotide fragments are overlapping, because they are generated with different rare-cutter enzymes that cut the target polynucleotides at different sites. The third polynucleotide fragments are partitioned into separate microwells 108 in a microdevice such that each microwell comprises a plurality of fragments, but only a single fragment with a particular sequence 109. The right-hand side of FIG. 2 illustrates three microwells (one is labeled 108), each containing three exemplary unique fragments 109, corresponding to the third polynucleotide fragments 107. Referring again to the right-hand side of FIG. 2, the left-most well contains fragments D1, E2, and F3, the middle well contains fragments E1, D2, and D3, and the right-most well contains fragments F1, F2, and E3.

With continued reference to FIG. 2, The partitioned fragments are then further fragmented, to generate a plurality of non-overlapping fourth polynucleotide fragments 110. The fourth polynucleotide fragments and the second polynucleotide fragments are overlapping, because they are generated by fragmenting the third and first fragments, respectively, which were generated with rare-cutter enzymes that cut the target polynucleotide at different sites, as described above. Referring again to the right-hand side of FIG. 2, each member of the fourth set of polynucleotide fragments is designated by its third fragment identifier (e.g., D1, E2, etc.), followed by a "−1" or a "−2". For example, third fragment D1 is fragmented to produce fourth fragments D1-1 and D1-2. Third fragment E2 is fragmented to produce fourth fragments E2-1 and E2-2, and so on. For the sake of simplicity, only two fourth fragments are shown for each third fragment. This is, of course, not meant to be limiting, as any number of fragments may be generated.

The fourth polynucleotides fragments are barcoded, and the barcoded sequences are pooled. Referring to the lower right-hand side of FIG. 2, the numbers [4], [5], and [6] represent three different barcode sequences used to label the fourth fragments 110. The labeled sequences are designated 111. Optionally, adapter sequences (not shown) are used to make the fourth fragments 110 compatible for ligation with the barcodes. The barcoding is performed while the fragments are still partitioned, before pooling. The pooled barcoded sequences are then sequenced.

The example above describes sequencing the barcoded second fragments separately from the barcoded fourth fragments. The barcoded second fragments and the barcoded fourth fragments may also be combined, and the combined sample may be sequenced. One or more steps of the process may be carried out in a device. The steps carried out in a device may be carried out in the same device or in different devices.

After sequencing, sequence contigs are assembled and the overlapping sequences between the second fragments and the fourth fragments are used to assemble the sequence of the genome.

Example 2

Pseudo-Random Fragmentation of Polynucleotides

A simulation was performed to evaluate the size distribution of fragments generated by a 6Mer cutter (StuI), a 4Mer cutter (CviQI), and two to seven 4Mer cutters. Random 1 Mbp DNA sequences were generated in silico and cuts were simulated based on the occurrence of the recognition sites for each of the restriction enzymes within the random sequences.

Figure 3:
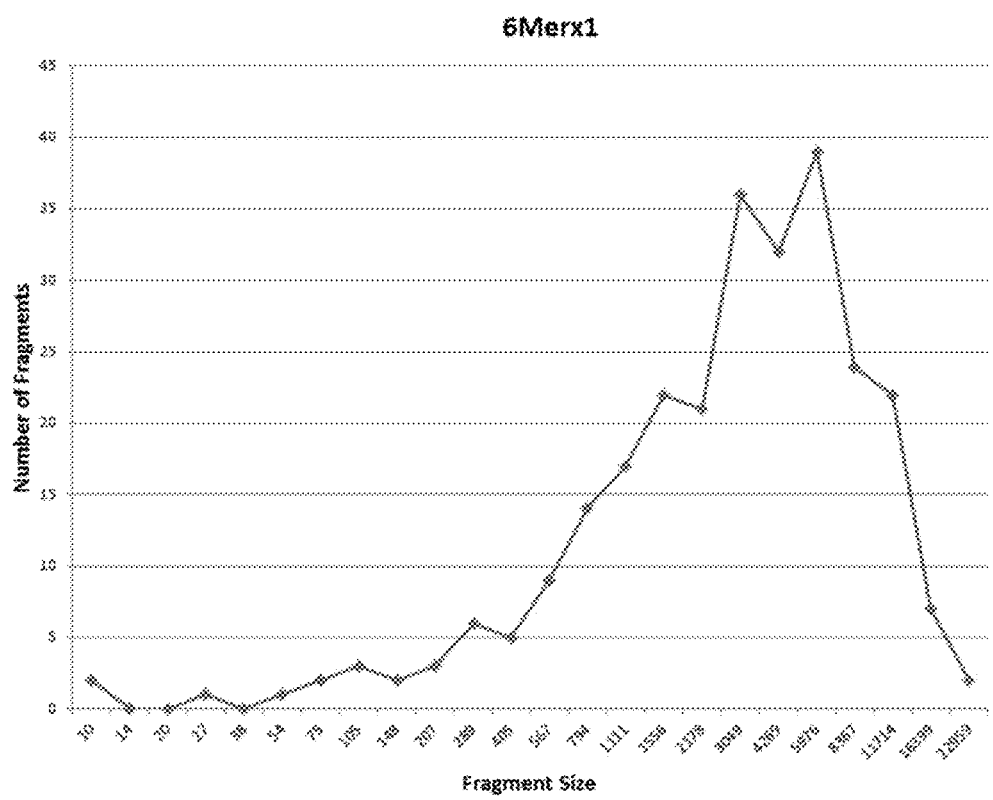
FIG. 3 shows a distribution of DNA fragment size after simulating generation of 1 Mbp random DNA sequences followed by cutting the sequences with a 6Mer cutter, StuI (AGG/CCT).

FIG. 3 shows the size distribution of a random 1 Mbp DNA sequence cut with the 6Mer cutter StuI (AGG/CCT). Fragments less than about 50 nucleotides were designated as "low yield," because they underutilize the read length capacity of sequencing instruments. Fragments less than about 200 nucleotides were designated as fragments likely to provide the most accurate data from today's sequencing technology. As described throughout this disclosure, this size range is in no way meant to be limiting, and the methods exemplified here, and described throughout this disclosure, may be used to generate fragments of any size range. Fragments from about 200 to about 400 nucleotides typically produce sequence data with systematic error for bases more than 100 bases from either fragment end. Fragments of more than about 400 nucleotides typically do not produce any useful sequence information for bases further than 200 bases from a fragment end, using today's sequencing technologies. However, this is expected to change, and the methods presented herein can be used to generate sequences of this size or larger.

As shown in FIG. 3, 3 of 271 fragments (1.5%) were considered low yield since they were 50 bases or smaller. Fourteen fragments (5%) were considered high accuracy since they were 200 bases or smaller (i.e., each base of the fragment is within 100 bases of a restriction site and could be sequenced with high accuracy). Eleven fragments (4%) were between 200 and 400 bases and would generate data that is both accurate (0-100 bases from each end) and inaccurate (100-200 bases from each end). The remaining 246 fragments (91%) were greater than 400 bases and would generate accurate (0-100), inaccurate (100-200) and no (>200 bases from a restriction site) sequence data. Overall only 5% of the 1 Mbp random sequence was within 100 bases from a restriction site and would generate accurate sequence data.

FIG. 4 shows the results from a second simulation using the 4Mer cutter CviQI (G/TAC), instead of StuI (the 6Mer cutter described above) to simulate cutting a random 1 Mbp DNA sequence. As shown in FIG. 4, the use of a restriction enzyme with a shorter recognition site results in more cuts, and the size distribution of the fragments is therefore shifted toward a smaller size range. In particular, as shown in FIG. 4, 18% of fragments were considered low yield since they were 50 bases or smaller. Thirty-eight percent of fragments were considered high accuracy since they were 200 bases or smaller (i.e., each base of the fragment was within 100 bases of a restriction site and could be sequenced with high accuracy). Twenty five percent of fragments were between 200 and 400 bases and would generate data that is both accurate (0-100 bases from each end) and inaccurate (100-200 bases from each end). The remaining fragments (37%) were greater than 400 bases and would generate accurate (0-100), inaccurate (100-200) and no (>200 bases from a restriction site) sequence data. Overall 56% of the 1 Mbp random sequence was within 100 bases from a restriction site and would generate accurate sequence data. Therefore, cutting the randomly generated 1 Mbp DNA sequence with CviQI resulted in a higher percentage of fragments with nucleotides within 100 nucleotides of a restriction site than cutting with StuI (i.e., 56% vs. 5%, respectively). Cutting with CviQI is therefore expected to provide more fragments that may be fully sequenced.

Figure 5:
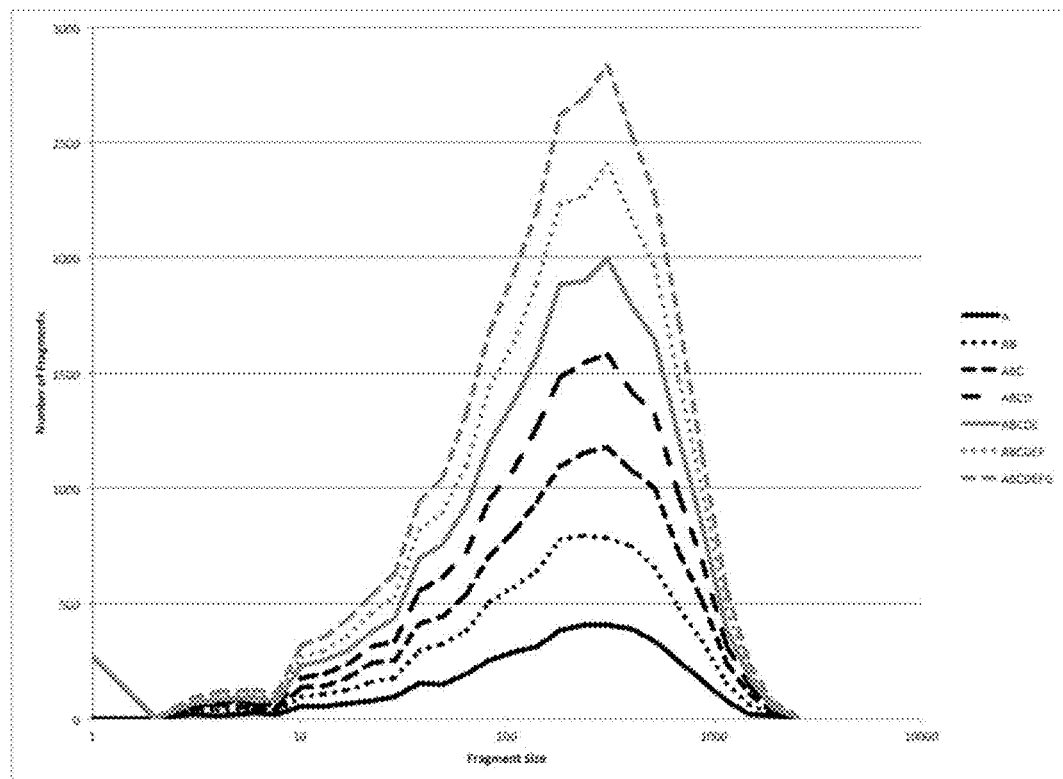
FIG. 5 shows a distribution of DNA fragment size after simulating the generation of a 1 Mbp random DNA sequence followed by cutting the sequences with seven 4Mer cutters: (1) CviQI (G/TAC), (2) BfaI (C/TAG), (3) HinP1I (G/CGC), (4) CviAII (C/ATG), (5) TaqαI (T/CGA), (6) MseI (T/TAA), and (7) MspI (C/CGG).

Next, simulated cuts were made in a random 1 Mbp DNA sequence using combinations of one to seven different 4Mer cutters. The 4Mer cutters were: (A) CviQI (G/TAC); (B) BfaI (C/TAG); (C) HinP1I (G/CGC); (D) CviAII (C/ATG); (E) TaqαI (T/CGA); (F) MseI (T/TAA); and (G) MspI (C/CGG). The results of these simulations are shown in FIG. 5. As shown in FIG. 5, increasing the number of 4Mer cutter enzymes, from one to seven, increases the number of fragments with nucleotides within 100 nucleotides of a restriction site. Therefore, cutting the randomly generated 1 Mbp DNA sequence with more than one 4Mer cutter results in more fragments that may be fully sequenced than cutting with a single 4Mer cutter.

The number of enzymes used to cut a sequence can be chosen so that a particular fraction of a target nucleotide (e.g., a genomic) sequence within 100 nucleotides of a restriction enzyme is achieved. For example, the fraction of a random genome within 100 nucleotides of a restriction site for a 4Mer cutter is equal to $1-0.44^x$, where x is the number of independent 4Mer cutters. Similarly, the fraction of a random genome within 100 nucleotides of a restriction site for a 5Mer cutter is equal to $1-0.25^x$, where x is the number of independent 5Mer cutters. For a 6Mer cutter, the fraction of a random genome within 100 nucleotides of a restriction site is equal to $1-0.95^x$, where x is the number of independent 6Mer cutters.

Table 1 shows the percentage of sequences with a length greater than 100 nucleotides for each of the seven enzymatic treatments described above. These sequences are considered those likely to result in missing data. Increasing the number of enzymes decreases the percentage of sequences greater than 100 nucleotides. The number of enzymes and their restriction site recognition length may be chosen in order to minimize the loss of sequence information from sequences greater than 100 nucleotides from a restriction site while also minimizing the generation of sequences less than 50 nucleotides, which are undesirable because the underutilize the read length capacity of sequencing instruments. The presence of these fragments may be minimized or avoided by selecting restriction enzymes that cut more rarely but at the potential price of reduced sequencing coverage of the DNA (i.e., more fragments may have bases >100 bases from a restriction site). These fragments may also be physically removed by a size selection step. Since these fragments are small and some fraction of the bases represented in the small fragments may be covered in larger fragments from other enzymes, the effect on coverage would likely be minimal.

The exemplary 4Mer cutter methods presented herein are optimized to provide fragments compatible with current DNA sequencing technology, which may achieve accurate read lengths up to about 100 nucleotides from the terminus of a fragment. One of ordinary skill in the art will readily recognize that other restriction enzymes (e.g., 5Mer cutters, 6Mer cutters, etc.) would be suitable for DNA sequencing technologies capable of accurately reading larger fragments of DNA (e.g., 300-400, or more nucleotides). The methods presented in this disclosure are, of course generalizable, and may be used to obtain DNA fragments of any size distribution compatible with present or future sequencing technology.

TABLE 1

Percentage of random 1 Mbp sequence more than 100 nucleotides from any restriction site. The letters in the first row refer to treatment with the following enzymes: (A) CviQI (G/TAC); (B) BfaI (C/TAG); (C) HinP1I (G/CGC); (D) CviAII (C/ATG); (E) TaqαI (T/CGA); (F) MseI (T/TAA); and (G) MspI (C/CGG).

| A | AB | ABC | ABCD | ABCDE | ABCDEF | ABCDEFG |
|---|----|-----|------|-------|--------|---------|
| 44.2% | 20.1% | 9.3% | 4.2% | 1.7% | 0.6% | 0.3% |

Example 3

High Yield Adapter Ligation by Restriction Enzyme-Mediated Recycling of Undesirable Side Products As described elsewhere herein, many downstream applications of the polynucleotide processing methods provided herein may utilize polynucleotide barcodes. An adapter may be used to provide compatible ends for the attachment of a barcode to a polynucleotide fragment (e.g., by ligation or PCR). In these cases, the desired products may be, for example:

[B]-[TPF]-[B], or
[B]-[A]-[TPF]-[A]-[B], where

[B] represents a barcode, [A] represents an adapter, and [TPF] represents a target polynucleotide fragment. However, in some cases, undesirable side products may form, for example, from the self ligation of barcodes, adapters, and/or target polynucleotide fragments. This example demonstrates one solution to this potential problem.

FIG. 6 shows a schematic of an implementation of the method described in this example. In the example shown in FIG. 6, three polynucleotide starting materials (Genomic DNA; Adapter 1; and Adapter 2) and three enzymes (MspI; NarI; and DNA Ligase) are contained within a partition. The restriction enzyme MspI (C/CGG) recognizes the CCGG sequence occurring within the Genomic DNA sequence and cuts the Genomic DNA sequence to generate a fragment of genomic DNA. If the reaction proceeds as intended, the fragment of genomic DNA is then ligated to Adapter 1 and Adapter 2, to generate a fragment of genomic DNA flanked by ligated adapters (FIG. 6, lower-left). This fragment with ligated adapters may then be ligated to DNA barcodes, which may also be present within the same partition (not shown).

However, the reaction described above may also result in several unwanted side products, including multimers produced by self-ligation of the fragmented genomic DNA and adapters (or other molecules, such as barcodes, which are not shown). For the sake of simplicity, FIG. 6 illustrates this concept by showing only self-ligation of fragmented genomic DNA and adapters.

One unwanted side product is a multimer of genomic DNA fragments. This may occur, for example, if genomic DNA fragments with compatible ends are ligated to each other after cutting. In FIG. 6, cutting of Genomic DNA with MspI generates compatible ends that may be ligated by the ligase present in the partition. Similarly, Adapter 1 and Adapter 2, as shown, have compatible ligatable ends, and may also be ligated to form multimers.

As indicated in FIG. 6, one solution to this problem is to pair one enzyme (in this example, MspI) with a second enzyme (in this example, NarI). In this example, MspI re-cuts genomic DNA multimers produced by self-ligation of genomic DNA fragments. Therefore, MspI recycles unwanted genomic DNA fragment multimers back into genomic DNA fragments, which may then be correctly ligated to the adapters. Similarly, Nan cuts multimers of Adapter 1 and Adapter 2 into monomers of Adapter 1 and monomers of Adapter 2, which may then be correctly ligated to genomic DNA fragments. This recycles unwanted adapter multimers back into the desired starting materials of Adapter 1 and Adapter 2.

The enzymes are chosen such that the desired product (i.e., the genomic DNA fragment with adapters on each end) does not contain a recognition site for either enzyme. Therefore, the product will not be re-cut by any enzyme contained within the partition. This process increases the yield of the desired product, while minimizing the number of unwanted side products and reducing the amount of starting material required to produce a desired amount of a product. As described in this disclosure, a pair of enzymes may be chosen so that one enzyme recognizes one undesirable side-product and regenerates a starting material and another recognizes another undesirable side product and regenerates another starting material, but neither enzyme recognizes the desired product. This can be done for an unlimited number of side products.

In general, one strategy for selecting such pairs is to choose two enzymes that create identical (or similar, ligatable) termini after cutting, but have recognition sequences of different lengths. FIG. 7 shows examples of such pairs of enzymes. The enzymes provided in FIG. 7A provide sticky ends, while those provided in FIG. 7B provide blunt ends.

The exemplary embodiment shown in FIG. 6 uses Genomic DNA and two adapters (Adapter 1 and Adapter 2) as starting materials. Therefore, in this embodiment, MspI is used not only to regenerate genomic DNA fragments after self-ligation, but also to generate the genomic DNA fragments in the first place, from Genomic DNA. Of course, this is optional, as one may introduce pre-fragmented genomic DNA into the partition and the method is still applicable.

Similarly, the embodiment shown in FIG. 6 shows two separate adapter molecules as starting materials. Adapter molecules may also be provided as a single polynucleotide sequence which is then cut by an enzyme contained within the partition (in this example, NarI) to generate ligation compatible ends for attachment to the fragmented genomic DNA. The method is also applicable to other polynucleotides described throughout this disclosure and to methods of attachment based on techniques other than ligation (e.g., attachment of an adapter or a barcode by PCR).

Pseudo-complimentary nucleotides that preferentially bind natural nucleotides over themselves (e.g., Biochemistry (1996) 35, 11170-11176; Nucleic Acids Research (1996) 15, 2470-2475), may also be used to minimize or avoid the formation of certain multimers, for example adapter-adapter multimers and barcode-barcode multimers. If adapters and/or barcodes (and/or other polynucleotides are synthesized using pseudo-complimentary nucleotides, they will prefer to hybridize with naturally occurring polynucleotide fragments (e.g., genomic DNA fragments) rather than themselves, therefore leading to a higher yield of the desired product.

Example 4

Provision of Reagents in Microcapsules and Directly in Microwells

Figure 8:
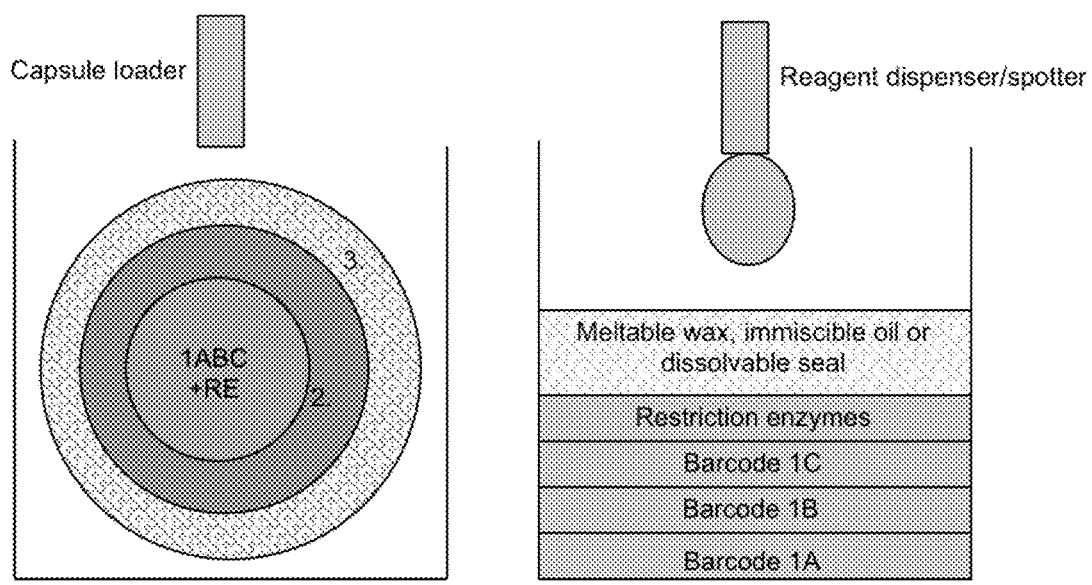
FIG. 8 shows a capsule containing reagents for barcoding of polynucleotide fragments in a microwell (left) and a microwell containing reagents for barcoding of polynucleotide fragments dispensed in a microwell and sealed to prevent evaporation (right).

As described throughout this disclosure, the polynucleotide processing methods described herein may involve the treatment of partitioned polynucleotides with a variety of reagents. These reagents may include, for example, restriction enzymes, ligases, phosphatases, kinases, barcodes, adapters, or any other reagent useful in polynucleotide processing or in a downstream application, such as sequencing. FIG. 8 shows two exemplary methods of providing reagents. On the left-hand side of FIG. 8, reagents are provided within a microcapsule. The microcapsule that is shown in FIG. 8 has an outer shell ("3"), an intermediate non-aqueous layer ("2") and an inner aqueous drop contained within the intermediate non-aqueous layer ("1ABC+ RE"). This droplet is made by a water-oil-water emulsion technique followed by polymerization of the outermost water layer ("3") to form a shell. Reagents are contained within the inner aqueous phase of the capsule. The left-hand side of FIG. 8 shows an exemplary embodiment with four reagents contained within the aqueous phase of the capsule, namely three barcode reagents (1A, 1B, and 1C), and a restriction enzyme ("RE"). The embodiment shown is merely exemplary. The reagents may be located in any part of the capsule.

The capsule is dispensed into a partition (e.g., a microwell). A target polynucleotide and a ligase are then added to the partition. The capsule is made to release its contents by exposure to a stimulus, such as a change in temperature, a solvent, or stirring. The restriction enzyme fragments the target polynucleotide and the ligase attaches the barcode reagents to the target polynucleotide fragments generated by the restriction enzyme.

The restriction digestion and ligation may proceed according to any of the methods described herein, for example by non-overlapping fragmentation techniques, by pseudo-random fragmentation methods, and/or by pairing of restriction enzymes to recycle unwanted side products into new starting products (e.g., target polynucleotide fragments and barcodes). Adapters may also be included within the microcapsule. The barcodes shown in FIG. 8 are modular. For example, barcode components 1A, 1B, and 1C may ligate to form barcode: [1A]-[1B]-[1C].

The right-hand side of FIG. 8 shows the same reagents dispensed into a microwell, followed by sealing with sealant (e.g., a wax or oil), to prevent evaporation before use. This approach may be substituted for the approach described above, where the reagents are placed within microcapsules. Both approaches are used to produce partitions (e.g., microwells) pre-loaded with reagents for DNA fragmentation and barcoding. In order to fragment and barcode DNA using reagents dispensed within a microwell, a user unseals a partition, and introduces a target polynucleotide and a ligase (or any other reagents applicable for the method the user is conducting). As described above, the restriction enzyme fragments the target polynucleotide and the ligase attaches the barcode reagents to the target polynucleotide fragments generated by the restriction enzyme. Of course, both approaches may be combined by placing certain reagents in the microwell and others in the microcapsule.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for nucleic acid preparation or analysis, comprising:
   (a) providing:
      (i) at least 1,000 gel beads;
      (ii) releasably attached to each of said at least 1,000 gel beads, at least 1,000 barcode molecules comprising identical barcode sequences that are distinct from barcode sequences of at least 1,000 barcode molecules releasably attached to any other gel bead of said at least 1,000 gel beads; and
      (iii) a plurality of cells each comprising a plurality of polynucleotide molecules;
   (b) generating a plurality of droplets, wherein at least 1,000 droplets of said plurality of droplets each comprise:
      (i) a single gel bead from said at least 1,000 gel beads; and
      (ii) a single cell from said plurality of cells; and
   (c) in each of said at least 1,000 droplets, using said plurality of polynucleotide molecules from said single cell and barcode molecules of said at least 1,000 barcode molecules from said single gel bead to generate a plurality of barcoded polynucleotide molecules, wherein said barcode molecules become detached from said gel bead.

2. The method of claim 1, wherein, prior to (c), said plurality of polynucleotide molecules are released from said single cell in each of said at least 1,000 droplets.

3. The method of claim 1, wherein said plurality of polynucleotide molecules are a plurality of messenger ribonucleic acid (mRNA) molecules.

4. The method of claim 3, wherein (c) comprises reverse transcribing said plurality of mRNA molecules in presence of said barcode molecules to generate said plurality of barcoded polynucleotide molecules.

5. The method of claim 1, further comprising causing said plurality of barcoded polynucleotide molecules to be released from said at least 1,000 droplets.

6. The method of claim 5, further comprising amplifying said plurality of barcoded polynucleotide molecules by nucleic acid amplification subsequent to releasing said plurality of barcoded polynucleotide molecules from said at least 1,000 droplets.

7. The method of claim 1, further comprising amplifying said plurality of barcoded polynucleotide molecules by nucleic acid amplification in each of said at least 1,000 droplets.

8. The method of claim 1, further comprising causing said plurality of barcoded polynucleotide molecules or derivatives thereof to be sequenced.

9. The method of claim 1, wherein a subset of said plurality of droplets does not include a cell.

10. The method of claim 1, wherein a subset of said plurality of droplets does not include a gel bead.

11. The method of claim 1, wherein in each of said at least 1,000 droplets, said barcode molecules are released from said single gel bead.

12. The method of claim 11, wherein each of said at least 1,000 droplets further comprise a reducing agent that depolymerizes said single gel bead, thereby releasing said barcode molecules.

13. The method of claim 1, wherein said at least 1,000 gel beads are formed by polymerization of droplets comprising said at least 1,000 barcode molecules.

14. The method of claim 1, wherein said at least 1,000 barcode molecules are disposed within said single gel bead.

15. The method of claim 1, wherein, in (a), said at least 1,000 gel beads are a subset of a plurality of gel beads.

16. The method of claim 15, wherein said plurality of gel beads comprises at least 10,000 gel beads.

17. The method of claim 1, wherein said at least 1,000 barcode molecules comprise combinatorial assemblies of sequences from sequence modules.

18. The method of claim 17, wherein each of said combinatorial assemblies comprises a combinatorial assembly of a first sequence and a second sequence.

19. The method of claim 17, wherein each of said combinatorial assemblies comprises a combinatorial assembly of a first sequence, a said second sequence, and a third sequence.

20. The method of claim 1, wherein said plurality of droplets comprises at least 10,000 droplets.

21. The method of claim 1, wherein said plurality of droplets comprises at least 100,000 droplets.

22. The method of claim 1, wherein said at least 1,000 gel beads comprises at least 10,000 gel beads, and wherein said at least 1,000 droplets comprises at least 10,000 droplets.

23. The method of claim 1, wherein said at least 1,000 gel beads comprises at least 100,000 gel beads, and wherein said at least 1,000 droplets comprises at least 100,000 droplets.

24. The method of claim 1, wherein said at least 1,000 barcode molecules are at least 10,000 barcode molecules.

25. The method of claim 1, wherein said at least 1,000 barcode molecules are at least 100,000 barcode molecules.

26. The method of claim 1, wherein said at least 1,000 barcode molecules are at least 1,000,000 barcode molecules.

27. The method of claim 1, wherein said plurality of polynucleotide molecules are from 10,000-100,000 polynucleotide molecules.

28. The method of claim 1, wherein said barcode molecules become detached from said gel bead before generation of said barcoded polynucleotide molecules.

29. The method of claim 1, wherein said barcode molecules become detached from said gel bead following generation of said barcoded polynucleotide molecules.

30. The method of claim 1, wherein said barcode molecules become detached from said gel bead during generation of said barcoded polynucleotide molecules.

* * * * *